United States Patent
Mouthon et al.

(10) Patent No.: US 10,639,301 B2
(45) Date of Patent: *May 5, 2020

(54) USE OF FLECAINIDE AS AN ANTI-CONNEXIN AGENT AND METHOD FOR POTENTIATING THE EFFECTS OF A PSYCHOTROPIC DRUG

(71) Applicant: Commissariat a L'Energie Atomique et Aux Energies Alternatives, Paris (FR)

(72) Inventors: Franck Mouthon, Boulogne-Billancourt (FR); Matthieu Charveriat, Issy les Moulineaux (FR)

(73) Assignee: Commissariat a L'Energie Atomique et Aux Energies Alternatives, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/138,641

(22) Filed: Sep. 21, 2018

(65) Prior Publication Data

US 2019/0008844 A1 Jan. 10, 2019

Related U.S. Application Data

(60) Division of application No. 15/667,999, filed on Aug. 3, 2017, now abandoned, which is a continuation of (Continued)

(30) Foreign Application Priority Data

Jul. 24, 2013 (EP) ..................................... 13306074

(51) Int. Cl.
*A61K 31/4458* (2006.01)
*A61K 45/06* (2006.01)
*A61K 31/165* (2006.01)

(52) U.S. Cl.
CPC ........ *A61K 31/4458* (2013.01); *A61K 31/165* (2013.01); *A61K 45/06* (2013.01)

(58) Field of Classification Search
CPC ... A61K 31/4458; A61K 31/165; A61K 45/06
See application file for complete search history.

(56) References Cited

U.S. PATENT DOCUMENTS

2011/0172188 A1    7/2011  Mouthon et al.
2013/0096067 A1    4/2013  Perrimon et al.

FOREIGN PATENT DOCUMENTS

JP    2001/253825 A    9/2001
JP    2012-502082 A    1/2012
(Continued)

OTHER PUBLICATIONS

Banitt et al., Resolution of Flecainide Acetate, N-(2-Piperidylmethyl)-2,5-Bis(2,2,2-Trifluoroethoxy)Benzam ide Acetate, and Antiarrhythmic Properties of the Enantiomers, J Med Chem 29 (1986) pp. 299-302.

(Continued)

*Primary Examiner* — San Ming R Hui
(74) *Attorney, Agent, or Firm* — Banner & Witcoff, Ltd.

(57) ABSTRACT

The present invention relates to the use of flecainide as an anti-connexin agent. This anti-connexin agent is advantageously used to potentiate the therapeutic effect of various psychotropic drugs. More specifically, the invention provides a combination product containing flecainide and modafinil.

8 Claims, 11 Drawing Sheets

Figure 1A:
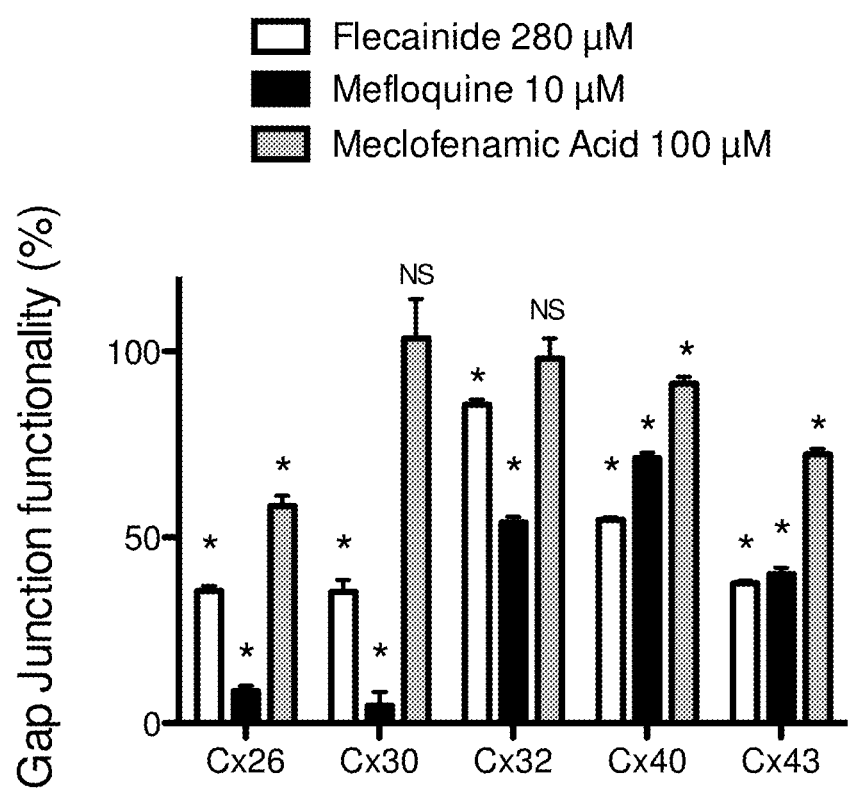

Specification includes a Sequence Listing.

Related U.S. Application Data application No. 14/907,221, filed as application No. PCT/EP2014/065975 on Jul. 24, 2014, now Pat. No. 9,750,734.

(56) References Cited

FOREIGN PATENT DOCUMENTS

| WO | 2005/039577 A1 | 5/2005 |
|---|---|---|
| WO | 2007/062186 A2 | 5/2007 |
| WO | 2010/029131 A1 | 3/2010 |

OTHER PUBLICATIONS

Beracochea et al., Impairment of Spontaneous Alternation Behavior in Sequential Test Procedures Following Mammillary Body Lesions in Mice: Evidence for Time-Dependent Interference-Related Memory Deficits, Behav Neurosci 101: pp. 187-197, 1987.
Gross et al., Stereoselective Disposition of Flecainide in Relation to the Sparteine/Debrisoquine Metaboliser Phenotype, Br J Clin Pharmacol 28 (1989) pp. 555-566.
Kroemer et al., Flecainide Enantiomers: Disposition in Human Subjects and Electrophysiologic Actions in Vitro, Clin Pharmacol Ther 46 (1989) pp. 584-590.
Smallwood et al., Electrophysiological Effects of Fecainide Enantiomers in Canine Purkinje Fibres, Naunyn Schmiedebergs Arch Pharmacol 339, (1989) pp. 625-629.
Lie-A-Huen et al., High-Performance Liquid Chromatographic Assay of Flecainide and Its Enantiomers in Serum, the Drug Monit 11 (1909) pp. 708-711.
Lie-A-Huen et al., The Action of Flecainide Acetate and Its Enantiomers on Mammalian Non-Myelinated Nerve Fibres, Pharm Weekbl Sci 11 (1989) pp. 92-94.
Alessi-Severini et al., High-Performance Liquid Chromatographic Determination of the Enantiomers of Flecainide in Human Plasma and Urine, J Pharm Sci 79 (1990) pp. 257-260.
Turgeon et al., Stereoselective Determination of Flecainide in Human Plasma by High-Performance Liquid Chromatography With Fluorescence Detection, J Pharm Sci 79 (1990) pp. 91-95.
Alessi-Severini et al., HPLC Analysis of Flecainide Enantiomers in Plasma: Comparison With Fluorescence Polarization Immunoassay, Clin Chem 37 (1991) pp. 111-112.
Simon et. al, The Stimulant Effect of Modafinil on Wakefulness is Not Associated With an Increase in Anxiety in Mice. A Comparison with Dexamphetamine. Psychopharmacology (Berl) 114: pp. 597-600. 1994.
Daleau, Effects of Antiarrhythmic Agents on Junctional Resistance of Guinea Pig Ventricular Cell Pairs, The Journal of Pharmacology and Experimental Therapeutics 284: pp. 1174-1179, 1998.
De Lecea et al., The Hypocretins: Hypothalamus-Specific Peptides With Neuroexcitatory Activity, Proc Natl Acad Sci US A 95: pp. 322-327, 1998.
Hanada et al., Quantitative Determination of Disopyramide, Verapamil and Flecainide Enantiomers in Rat Plasma and Tissues by High-Performance Liquid Chromatography, J Chromatogr B Biomed Sci Appl 710, pp. 129-135, 1998.
Sakurai et al., Orexins and Orexin receptors: A Family of Hypothalamic Neuropeptides and G Protein-Coupled Receptors That Regulate Feeding Behavior, Cell 92: 1 Page Following 696. 1998.
Chemelli et al., Narcolepsy in Orexin Knockout Mice: Molecular Genetics of Sleep Regulation, Cell 98: pp. 437-451, 1999.
Lin et al., The Sleep Disorder Canine Narcolepsy is Caused by a Mutation in the Hypocretin (Orexin) Receptor 2 Gene, Cell 98: pp. 365-376, 1999.
Beracochea et al., First Evidence of a Delay-Dependent Working Memory-Enhancing Effect of Modafinil in Mice. Neuroreport 12: pp. 375-378. 2001.
Harks et al., Fenmates: A Novel Class of Reversible Gap Junction Blockers, the Journal of Pharmacology and Experimental Therapeutics 298: pp. 1033-1041. 2001.

Mehvar et al., Impact of Stereoselectivity on the Pharmacokinetics and Pharmacodynamics of Antiarrhythmic Drugs, Clin Pharmacokinet 41 (2002) pp. 533-558.
Parmentier et al., Anatomical, Physiological, and Pharmacological Characteristics of Histidine Decarboxylase Knock-Out Mice: Evidence for the Role of Brain Histamine in Behavioral and Sleep-Wake Control, J Neurosci 22 (2002) pp. 7695-7711.
Beracochea et al., Enhancement of Learning Processes Following an Acute Modafinil Injection in Mice, Pharmacology, Biochemistry, and Behavior 76: pp. 473-479, 2003.
Cruikshank et al., Potenet Block of Cx36 and Cx50 Gap Junction Channels by Mefloquine, Proc Natl Acad Sci USA 101: pp. 12364-12369, 2004.
Dhein, Pharmacology of GAP Junctions in the Cardiovascular System, Cardiovasc Res 62: pp. 287-298, 2004.
Nakase et al., Gap Junctions and Neurological Disorders of the Central Nervous System. Biochim Biophys Acta 1662: pp. 149-158, 2004.
Mignot et al., Emerging Therapies in Narcolepsy-Cataplexy, Sleep 28, pp. 754-763, 2005.
Del Corsso et al., Transfection of Mammalian Cells with Connexins and Measurement of Voltage Sensitivity of Their Gap Junctions, Nat Protoc 1: pp. 1799-1809, 2006.
Fujiki et al., Sex Difference in Body Weight Gain and Leptin Signaling in Hypocretin/Orexin Deficient Mouse Models, Peptides 27 (2006) pp. 2326-2331.
Laird, Life Cycle of Connexins in Health and Disease, Biochem J 394: pp. 527-543, 2006.
Dauvilliers et al., Narcolepsy With Cataplexy, Lancet 369, pp. 499-511, 2007.
Lin et al., An Inverse Agonist of the Histamine H3 Receptor Improves Wakefulness in Narcolepsy: Studies in Orexin -/- Mice and Patients. Neurobiology of Disease 30: pp. 74-83, 2008.
Minzenberg et al., Modafinil: A Review of Nerochemical Actions and Effects on Cognition. Neuropsychopharmacology 33: pp. 1477-1502, 2008.
Anaclet et al., Orexin/Hypocretin and Histamine: Distinct Roles in the Control of Wakefulness Demonstrated Using Knock-Out Mouse Models, The Journal of Neuroscience: The Official Journal of the Society for Neuroscience 29: pp. 14423-14438, 2009.
Dubey et al., A Novel Study of Screening and Confirmation of Modafinil, Adrafinil and Their Metabolite Modafinilic Acid Under EI-GC-MS and ESL-LC-MS-MS Ionaztion, Indian Journal of Pharmacology 41: pp. 278-283, 2009.
Durham et al., Neurological Mechanisms of Migraine: Potential of the Gap-Junction Modulator Tonabersat in Prevention of Migraine. Cephalagia 29 Suppl 2: pp. 1-6, 2009.
Boulos et al., Current Evaluation and Management of Excessive Daytime Sleepiness, Can J Neurol Sci 37, pp. 167-176, 2010.
Traynelis et al., Glutamate Receptor Ion Channels: Structure, Regulation, and Function; Pharmacological Reviews 62: pp. 405-496, 2010.
Takeuchi et al., Blockade of Gap Junction Hemichannel Suppresses Disease Progression in Mouse Models of Amyotrophic Lateral Sclerosis and Alzheimer's Disease, PLoS One 6: e21108, 2011.
Lin et al., The Waking Brain: An Update, Cell Mol Life Sci 68, pp. 2499-2512, 2011.
Lin et al., Histamine H3 Receptors and Sleep-Wake Regulation, The Journal of Pharmacology and Experimental Therapeutics 336: pp. 17-23, 2011.
Gotter et al., International Union of Basic and Clinical Pharmacology. LXXXVI. Orexin Receptor Function, Nomenclature and Pharmacology, Pharmacological Reviews 64: pp. 389-420.
Ishizuka et al., Action of Modafinil Through Histaminergic and Orexinergic Neurons, Vitamins and Hormones 89: pp. 259-278, 2012.
Patel et al., Gap Junction Inhibition Prevents DRYG-Induced Liver Toxicty and Fulminant Hepatic Failure, Nature Biotechnology 30: pp. 179-183, 2012.
Davidson et al., Connexin Hemichannel Blockade is Neuroprotective After, but Not During, Global Cerebral Ischemia in Near-Term Feetal Sheep, Experimental Neurology, 2013.

(56) References Cited

OTHER PUBLICATIONS

Tong et al., Role of Heteromeric Gap Junctions in the Cytotoxicity of Cisplatin, Toxicology 310C: pp. 53-60.
Waxman et al., Sodium Channel Blockers and Axonal Protection in Neuroin Flammatory Disease, Brain vol. 128 No. 1, Guarantors of Brain 2005, pp. 5-6.
Rueschenschmidt et al., Characterization of a Fast Transient Outward Current in Neocortical Neurons From Epilepsy Patients, Journal of Neuroscience Research vol. 75, 2004, pp. 807-816.
Desaphy et al., Dramatic Improvement of Myotonia Permanens With Flecainide: A Two Case Report of a Possible Bench-to-Bedside Pharmacogenetics Strategy, European Journal of Clinical Pharmacology, 2013, vol. 69, 1037-1039.
Gao et al., Expression of Voltage-Gated Sodium Channel a Subunit in Human Ovarian Cancer, Oncology Reports, 2010, vol. 23, pp. 1293-1299.
Shigemizu et al., Using Functional Signatures to Identify Repositioned Drugs for Breast, Myelogenous Leukemia and Prostate Cancer, PLoS Computational Biology, 2012, vol. 8, Issue 2, pp. 1-9.
Yildirim et al., Voltage-Gated Sodium Channel Activity Promotes Prostate Cancer Metastasis in Vivo, Cancer Letters 2012, vol. 323, pp. 58-61.
Roger et al., Voltage-Gated Sodium Channels: New Targets in Cancer Therapy? Current Pharmaceutical Design, vol. 12, 2006, pp. 3681-3695.
Hernandez-Plata et al., Overexpression of Nav1.6 Channels is Associated With the Invasion Capacity of Human Cervical Cancer, Int. J. Cancer, vol. 130, 2012, pp. 2013-2023.
Trivedi et al., Cellular His Assays for Pharmacological Characterization of Nav1.7 Modulators, Assay and Drug Development Technologies, vol. 6, Issue 2, pp. 167-179, 2008.
International Search Report Issued in Corresponding International Application No. PCT/EP2014/065975, dated Sep. 16, 2014.
European Search Report Issued in Corresponding European Application No. EP 13 30 6074, dated Sep. 23, 2013.
Nojima et al., Selective Inhibition of Human TNF-a Action by Flecainide Acetate, an Anitarrhythmic Drug, Physiol. Chem. Phys & Med. NMR 27 (1995) pp. 77-89.
Tubman et al, Ventricular Tachycardia Associated with Coxsackie B4 Virus Infection, Actra Paediatr Scand 79 (1990), pp. 572-575.
Japanese Circulation Journal, vol. 65 Suppl. 1-A (2001).
The Japanese Journal of Physiology, vol. 51 Suppl. 2001: S150.

Two-way ANOVA, repeated measures by both factors
*p<0,05 vs Vehicule
p<0,05 vs Modafinil 64

SEQUENCE LISTING

<160> NUMBER OF SEQ ID NOS: 21

<210> SEQ ID NO 1
<211> LENGTH: 205
<212> TYPE: PRT
<213> ORGANISM: homo sapiens
<220> FEATURE:
<221> NAME/KEY: MISC_FEATURE
<223> OTHER INFORMATION: Cx23 (A6NN92)

<400> SEQUENCE: 1

Met Ser Leu Asn Tyr Ile Lys Asn Phe Tyr Glu Gly Cys Val Lys Pro

```
                1               5                    10                     15
            Pro Thr Val Ile Gly Gln Phe His Thr Leu Phe Phe Gly Ser Ile Arg
                            20                  25                  30

Ile Phe Phe Leu Gly Val Leu Gly Phe Ala Val Tyr Gly Asn Glu Ala
                            35                  40                  45

Leu His Phe Ile Cys Asp Pro Asp Lys Arg Glu Val Asn Leu Phe Cys
                50                      55                  60

Tyr Asn Gln Phe Arg Pro Ile Thr Pro Gln Val Ser Phe Ser Ala Leu
            65                      70                  75                  80

Gln Leu Val Ile Val Leu Val Pro Gly Ala Leu Phe His Leu Tyr Ala
                                85                  90                  95

Ala Cys Lys Ser Ile Asn Gln Glu Cys Ile Leu Gln Lys Pro Ile Tyr
                            100                 105                 110

Thr Ile Ile Tyr Ile Leu Ser Val Leu Leu Arg Ile Ser Leu Ala Ala
                            115                 120                 125

Ile Ala Phe Trp Leu Gln Ile Tyr Leu Phe Gly Phe Gln Val Lys Ser
                        130                 135                 140

Leu Tyr Leu Cys Asp Ala Arg Ser Leu Gly Glu Asn Met Ile Ile Arg
            145                 150                 155                 160

Cys Met Val Pro Glu His Phe Glu Lys Thr Ile Phe Leu Ile Ala Ile
                                165                 170                 175

Asn Thr Phe Thr Thr Ile Thr Ile Leu Leu Phe Val Ala Glu Ile Phe
                            180                 185                 190

Glu Ile Ile Phe Arg Arg Leu Tyr Phe Pro Phe Arg Gln
                        195                 200                 205

<210> SEQ ID NO 2
<211> LENGTH: 223
<212> TYPE: PRT
<213> ORGANISM: homo sapiens
<220> FEATURE:
<221> NAME/KEY: MISC_FEATURE
<223> OTHER INFORMATION: Cx25 (NP_940970.1)

<400> SEQUENCE: 2

Met Ser Trp Met Phe Leu Arg Asp Leu Leu Ser Gly Val Asn Lys Tyr
            1               5                   10                  15

Ser Thr Gly Thr Gly Trp Ile Trp Leu Ala Val Val Phe Val Phe Arg
                            20                  25                  30

Leu Leu Val Tyr Met Val Ala Ala Glu His Val Trp Lys Asp Glu Gln
                        35                  40                  45

Lys Glu Phe Glu Cys Asn Ser Arg Gln Pro Gly Cys Lys Asn Val Cys
                50                  55                  60

Phe Asp Asp Phe Phe Pro Ile Ser Gln Val Arg Leu Trp Ala Leu Gln
            65                  70                  75                  80

Leu Ile Met Val Ser Thr Pro Ser Leu Leu Val Val Leu His Val Ala
                            85                  90                  95

Tyr His Glu Gly Arg Glu Lys Arg His Arg Lys Lys Leu Tyr Val Ser
                            100                 105                 110

Pro Gly Thr Met Asp Gly Gly Leu Trp Tyr Ala Tyr Leu Ile Ser Leu
                        115                 120                 125

Ile Val Lys Thr Gly Phe Glu Ile Gly Phe Leu Val Leu Phe Tyr Lys
                        130                 135                 140

Leu Tyr Asp Gly Phe Ser Val Pro Tyr Leu Ile Lys Cys Asp Leu Lys
            145                 150                 155                 160
```

```
Pro Cys Pro Asn Thr Val Asp Cys Phe Ile Ser Lys Pro Thr Glu Lys
            165                 170                 175

Thr Ile Phe Ile Leu Phe Leu Val Ile Thr Ser Cys Leu Cys Ile Val
            180                 185                 190

Leu Asn Phe Ile Glu Leu Ser Phe Leu Val Leu Lys Cys Phe Ile Lys
            195                 200                 205

Cys Cys Leu Gln Lys Tyr Leu Lys Lys Pro Gln Val Leu Ser Val
            210                 215                 220

<210> SEQ ID NO 3
<211> LENGTH: 226
<212> TYPE: PRT
<213> ORGANISM: homo sapiens
<220> FEATURE:
<221> NAME/KEY: MISC_FEATURE
<223> OTHER INFORMATION: Cx26 (P29033.3)

<400> SEQUENCE: 3

Met Asp Trp Gly Thr Leu Gln Thr Ile Leu Gly Gly Val Asn Lys His
1               5                   10                  15

Ser Thr Ser Ile Gly Lys Ile Trp Leu Thr Val Leu Phe Ile Phe Arg
            20                  25                  30

Ile Met Ile Leu Val Val Ala Ala Lys Glu Val Trp Gly Asp Glu Gln
            35                  40                  45

Ala Asp Phe Val Cys Asn Thr Leu Gln Pro Gly Cys Lys Asn Val Cys
50                  55                  60

Tyr Asp His Tyr Phe Pro Ile Ser His Ile Arg Leu Trp Ala Leu Gln
65                  70                  75                  80

Leu Ile Phe Val Ser Thr Pro Ala Leu Leu Val Ala Met His Val Ala
            85                  90                  95

Tyr Arg Arg His Glu Lys Lys Arg Lys Phe Ile Lys Gly Glu Ile Lys
            100                 105                 110

Ser Glu Phe Lys Asp Ile Glu Glu Ile Lys Thr Gln Lys Val Arg Ile
            115                 120                 125

Glu Gly Ser Leu Trp Trp Thr Tyr Thr Ser Ser Ile Phe Phe Arg Val
            130                 135                 140

Ile Phe Glu Ala Ala Phe Met Tyr Val Phe Tyr Val Met Tyr Asp Gly
145                 150                 155                 160

Phe Ser Met Gln Arg Leu Val Lys Cys Asn Ala Trp Pro Cys Pro Asn
            165                 170                 175

Thr Val Asp Cys Phe Val Ser Arg Pro Thr Glu Lys Thr Val Phe Thr
            180                 185                 190

Val Phe Met Ile Ala Val Ser Gly Ile Cys Ile Leu Leu Asn Val Thr
            195                 200                 205

Glu Leu Cys Tyr Leu Leu Ile Arg Tyr Cys Ser Gly Lys Ser Lys Lys
            210                 215                 220

Pro Val
225

<210> SEQ ID NO 4
<211> LENGTH: 261
<212> TYPE: PRT
<213> ORGANISM: homo sapiens
<220> FEATURE:
<221> NAME/KEY: MISC_FEATURE
<223> OTHER INFORMATION: Cx30 (NP_001103689.1)

<400> SEQUENCE: 4
```

Met Asp Trp Gly Thr Leu His Thr Phe Ile Gly Val Asn Lys His
1               5                   10                  15

Ser Thr Ser Ile Gly Lys Val Trp Ile Thr Val Ile Phe Ile Phe Arg
            20                  25                  30

Val Met Ile Leu Val Val Ala Ala Gln Glu Val Trp Gly Asp Glu Gln
        35                  40                  45

Glu Asp Phe Val Cys Asn Thr Leu Gln Pro Gly Cys Lys Asn Val Cys
    50                  55                  60

Tyr Asp His Phe Phe Pro Val Ser His Ile Arg Leu Trp Ala Leu Gln
65                  70                  75                  80

Leu Ile Phe Val Ser Thr Pro Ala Leu Leu Val Ala Met His Val Ala
                85                  90                  95

Tyr Tyr Arg His Glu Thr Thr Arg Lys Phe Arg Arg Gly Glu Lys Arg
            100                 105                 110

Asn Asp Phe Lys Asp Ile Glu Asp Ile Lys Lys Gln Lys Val Arg Ile
        115                 120                 125

Glu Gly Ser Leu Trp Trp Thr Tyr Thr Ser Ser Ile Phe Phe Arg Ile
    130                 135                 140

Ile Phe Glu Ala Ala Phe Met Tyr Val Phe Tyr Phe Leu Tyr Asn Gly
145                 150                 155                 160

Tyr His Leu Pro Trp Val Leu Lys Cys Gly Ile Asp Pro Cys Pro Asn
                165                 170                 175

Leu Val Asp Cys Phe Ile Ser Arg Pro Thr Glu Lys Thr Val Phe Thr
            180                 185                 190

Ile Phe Met Ile Ser Ala Ser Val Ile Cys Met Leu Leu Asn Val Ala
        195                 200                 205

Glu Leu Cys Tyr Leu Leu Leu Lys Val Cys Phe Arg Arg Ser Lys Arg
    210                 215                 220

Ala Gln Thr Gln Lys Asn His Pro Asn His Ala Leu Lys Glu Ser Lys
225                 230                 235                 240

Gln Asn Glu Met Asn Glu Leu Ile Ser Asp Ser Gly Gln Asn Ala Ile
                245                 250                 255

Thr Gly Phe Pro Ser
            260

<210> SEQ ID NO 5
<211> LENGTH: 279
<212> TYPE: PRT
<213> ORGANISM: homo sapiens
<220> FEATURE:
<221> NAME/KEY: MISC_FEATURE
<223> OTHER INFORMATION: Cx30.2 (NP_853516.1)

<400> SEQUENCE: 5

Met Cys Gly Arg Phe Leu Arg Arg Leu Leu Ala Glu Glu Ser Arg Arg
1               5                   10                  15

Ser Thr Pro Val Gly Arg Leu Leu Leu Pro Val Leu Leu Gly Phe Arg
            20                  25                  30

Leu Val Leu Leu Ala Ala Ser Gly Pro Gly Val Tyr Gly Asp Glu Gln
        35                  40                  45

Ser Glu Phe Val Cys His Thr Gln Gln Pro Gly Cys Lys Ala Ala Cys
    50                  55                  60

Phe Asp Ala Phe His Pro Leu Ser Pro Leu Arg Phe Trp Val Phe Gln
65                  70                  75                  80

Val Ile Leu Val Ala Val Pro Ser Ala Leu Tyr Met Gly Phe Thr Leu
                85                  90                  95

-continued

Tyr His Val Ile Trp His Trp Glu Leu Ser Gly Lys Gly Lys Glu Glu
                    100                 105                 110

Glu Thr Leu Ile Gln Gly Arg Glu Gly Asn Thr Asp Val Pro Gly Ala
            115                 120                 125

Gly Ser Leu Arg Leu Leu Trp Ala Tyr Val Ala Gln Leu Gly Ala Arg
        130                 135                 140

Leu Val Leu Glu Gly Ala Ala Leu Gly Leu Gln Tyr His Leu Tyr Gly
145                 150                 155                 160

Phe Gln Met Pro Ser Ser Phe Ala Cys Arg Arg Glu Pro Cys Leu Gly
                    165                 170                 175

Ser Ile Thr Cys Asn Leu Ser Arg Pro Ser Gly Lys Thr Ile Phe Leu
            180                 185                 190

Lys Thr Met Phe Gly Val Ser Gly Phe Cys Leu Leu Phe Thr Phe Leu
        195                 200                 205

Glu Leu Val Leu Leu Gly Leu Gly Arg Trp Trp Arg Thr Trp Lys His
210                 215                 220

Lys Ser Ser Ser Lys Tyr Phe Leu Thr Ser Glu Ser Thr Arg Arg
225                 230                 235                 240

His Lys Lys Ala Thr Asp Ser Leu Pro Val Val Glu Thr Lys Glu Gln
                    245                 250                 255

Phe Gln Glu Ala Val Pro Gly Arg Ser Leu Ala Gln Glu Lys Gln Arg
            260                 265                 270

Pro Val Gly Pro Arg Asp Ala
        275

<210> SEQ ID NO 6
<211> LENGTH: 266
<212> TYPE: PRT
<213> ORGANISM: homo sapiens
<220> FEATURE:
<221> NAME/KEY: MISC_FEATURE
<223> OTHER INFORMATION: Cx30.3 (NP_694944.1)

<400> SEQUENCE: 6

Met Asn Trp Ala Phe Leu Gln Gly Leu Leu Ser Gly Val Asn Lys Tyr
1               5                   10                  15

Ser Thr Val Leu Ser Arg Ile Trp Leu Ser Val Val Phe Ile Phe Arg
            20                  25                  30

Val Leu Val Tyr Val Val Ala Ala Glu Glu Val Trp Asp Asp Glu Gln
        35                  40                  45

Lys Asp Phe Val Cys Asn Thr Lys Gln Pro Gly Cys Pro Asn Val Cys
50                  55                  60

Tyr Asp Glu Phe Phe Pro Val Ser His Val Arg Leu Trp Ala Leu Gln
65                  70                  75                  80

Leu Ile Leu Val Thr Cys Pro Ser Leu Leu Val Val Met His Val Ala
                    85                  90                  95

Tyr Arg Glu Glu Arg Glu Arg Lys His His Leu Lys His Gly Pro Asn
                    100                 105                 110

Ala Pro Ser Leu Tyr Asp Asn Leu Ser Lys Lys Arg Gly Gly Leu Trp
            115                 120                 125

Trp Thr Tyr Leu Leu Ser Leu Ile Phe Lys Ala Ala Val Asp Ala Gly
        130                 135                 140

Phe Leu Tyr Ile Phe His Arg Leu Tyr Lys Asp Tyr Asp Met Pro Arg
145                 150                 155                 160

Val Val Ala Cys Ser Val Glu Pro Cys Pro His Thr Val Asp Cys Tyr

```
            165                 170                 175
Ile Ser Arg Pro Thr Glu Lys Lys Val Phe Thr Tyr Phe Met Val Thr
                180                 185                 190

Thr Ala Ala Ile Cys Ile Leu Leu Asn Leu Ser Glu Val Phe Tyr Leu
            195                 200                 205

Val Gly Lys Arg Cys Met Glu Ile Phe Gly Pro Arg His Arg Arg Pro
210                 215                 220

Arg Cys Arg Glu Cys Leu Pro Asp Thr Cys Pro Pro Tyr Val Leu Ser
225                 230                 235                 240

Gln Gly Gly His Pro Glu Asp Gly Asn Ser Val Leu Met Lys Ala Gly
                245                 250                 255

Ser Ala Pro Val Asp Ala Gly Gly Tyr Pro
                260                 265

<210> SEQ ID NO 7
<211> LENGTH: 270
<212> TYPE: PRT
<213> ORGANISM: homo sapiens
<220> FEATURE:
<221> NAME/KEY: MISC_FEATURE
<223> OTHER INFORMATION: Cx31 (NP_001005752.1)

<400> SEQUENCE: 7

Met Asp Trp Lys Thr Leu Gln Ala Leu Leu Ser Gly Val Asn Lys Tyr
1               5                   10                  15

Ser Thr Ala Phe Gly Arg Ile Trp Leu Ser Val Val Phe Val Phe Arg
            20                  25                  30

Val Leu Val Tyr Val Val Ala Ala Glu Arg Val Trp Gly Asp Glu Gln
        35                  40                  45

Lys Asp Phe Asp Cys Asn Thr Lys Gln Pro Gly Cys Thr Asn Val Cys
50                  55                  60

Tyr Asp Asn Tyr Phe Pro Ile Ser Asn Ile Arg Leu Trp Ala Leu Gln
65                  70                  75                  80

Leu Ile Phe Val Thr Cys Pro Ser Leu Leu Val Ile Leu His Val Ala
                85                  90                  95

Tyr Arg Glu Glu Arg Glu Arg Arg His Arg Gln Lys His Gly Asp Gln
            100                 105                 110

Cys Ala Lys Leu Tyr Asp Asn Ala Gly Lys Lys His Gly Gly Leu Trp
        115                 120                 125

Trp Thr Tyr Leu Phe Ser Leu Ile Phe Lys Leu Ile Ile Glu Phe Leu
130                 135                 140

Phe Leu Tyr Leu Leu His Thr Leu Trp His Gly Phe Asn Met Pro Arg
145                 150                 155                 160

Leu Val Gln Cys Ala Asn Val Ala Pro Cys Pro Asn Ile Val Asp Cys
                165                 170                 175

Tyr Ile Ala Arg Pro Thr Glu Lys Lys Ile Phe Thr Tyr Phe Met Val
            180                 185                 190

Gly Ala Ser Ala Val Cys Ile Val Leu Thr Ile Cys Glu Leu Cys Tyr
        195                 200                 205

Leu Ile Cys His Arg Val Leu Arg Gly Leu His Lys Asp Lys Pro Arg
210                 215                 220

Gly Gly Cys Ser Pro Ser Ser Ala Ser Arg Ala Ser Thr Cys Arg
225                 230                 235                 240

Cys His His Lys Leu Val Glu Ala Gly Glu Val Asp Pro Asp Pro Gly
                245                 250                 255
```

```
Asn Asn Lys Leu Gln Ala Ser Ala Pro Asn Leu Thr Pro Ile
            260                 265                 270
```

<210> SEQ ID NO 8
<211> LENGTH: 273
<212> TYPE: PRT
<213> ORGANISM: homo sapiens
<220> FEATURE:
<221> NAME/KEY: MISC_FEATURE
<223> OTHER INFORMATION: Cx31.1 (NP_005259.1)

<400> SEQUENCE: 8

```
Met Asn Trp Ser Ile Phe Glu Gly Leu Leu Ser Gly Val Asn Lys Tyr
1               5                   10                  15

Ser Thr Ala Phe Gly Arg Ile Trp Leu Ser Leu Val Phe Ile Phe Arg
            20                  25                  30

Val Leu Val Tyr Leu Val Thr Ala Glu Arg Val Trp Ser Asp Asp His
        35                  40                  45

Lys Asp Phe Asp Cys Asn Thr Arg Gln Pro Gly Cys Ser Asn Val Cys
    50                  55                  60

Phe Asp Glu Phe Phe Pro Val Ser His Val Arg Leu Trp Ala Leu Gln
65                  70                  75                  80

Leu Ile Leu Val Thr Cys Pro Ser Leu Leu Val Val Met His Val Ala
                85                  90                  95

Tyr Arg Glu Val Gln Glu Lys Arg His Arg Glu Ala His Gly Glu Asn
            100                 105                 110

Ser Gly Arg Leu Tyr Leu Asn Pro Gly Lys Lys Arg Gly Gly Leu Trp
        115                 120                 125

Trp Thr Tyr Val Cys Ser Leu Val Phe Lys Ala Ser Val Asp Ile Ala
    130                 135                 140

Phe Leu Tyr Val Phe His Ser Phe Tyr Pro Lys Tyr Ile Leu Pro Pro
145                 150                 155                 160

Val Val Lys Cys His Ala Asp Pro Cys Pro Asn Ile Val Asp Cys Phe
                165                 170                 175

Ile Ser Lys Pro Ser Glu Lys Asn Ile Phe Thr Leu Phe Met Val Ala
            180                 185                 190

Thr Ala Ala Ile Cys Ile Leu Leu Asn Leu Val Glu Leu Ile Tyr Leu
        195                 200                 205

Val Ser Lys Arg Cys His Glu Cys Leu Ala Ala Arg Lys Ala Gln Ala
    210                 215                 220

Met Cys Thr Gly His His Pro His Gly Thr Thr Ser Ser Cys Lys Gln
225                 230                 235                 240

Asp Asp Leu Leu Ser Gly Asp Leu Ile Phe Leu Gly Ser Asp Ser His
                245                 250                 255

Pro Pro Leu Leu Pro Asp Arg Pro Arg Asp His Val Lys Lys Thr Ile
            260                 265                 270

Leu
```

<210> SEQ ID NO 9
<211> LENGTH: 294
<212> TYPE: PRT
<213> ORGANISM: homo sapiens
<220> FEATURE:
<221> NAME/KEY: misc_feature
<223> OTHER INFORMATION: Cx31.9 (NP_689343.3)

<400> SEQUENCE: 9

```
Met Gly Glu Trp Ala Phe Leu Gly Ser Leu Leu Asp Ala Val Gln Leu
```

```
            1               5                  10                 15
        Gln Ser Pro Leu Val Gly Arg Leu Trp Leu Val Val Met Leu Ile Phe
                        20                 25                 30

Arg Ile Leu Val Leu Ala Thr Val Gly Gly Ala Val Phe Glu Asp Glu
                        35                 40                 45

Gln Glu Glu Phe Val Cys Asn Thr Leu Gln Pro Gly Cys Arg Gln Thr
                50                  55                 60

Cys Tyr Asp Arg Ala Phe Pro Val Ser His Tyr Arg Phe Trp Leu Phe
         65                  70                 75                 80

His Ile Leu Leu Leu Ser Ala Pro Pro Val Leu Phe Val Val Tyr Ser
                        85                 90                 95

Met His Arg Ala Gly Lys Glu Ala Gly Ala Glu Ala Ala Ala Ala Gln
                       100                105                110

Cys Ala Pro Gly Leu Pro Glu Ala Gln Cys Ala Pro Cys Ala Leu Arg
                       115                120                125

Ala Arg Arg Ala Arg Cys Tyr Leu Leu Ser Val Ala Leu Arg Leu
                       130                135                140

Leu Ala Glu Leu Thr Phe Leu Gly Gly Gln Ala Leu Leu Tyr Gly Phe
        145                 150                155                160

Arg Val Ala Pro His Phe Ala Cys Ala Gly Pro Cys Pro His Thr
                           165                170                175

Val Asp Cys Phe Val Ser Arg Pro Thr Glu Lys Thr Val Phe Val Leu
                       180                185                190

Phe Tyr Phe Ala Val Gly Leu Leu Ser Ala Leu Leu Ser Val Ala Glu
                       195                200                205

Leu Gly His Leu Leu Trp Lys Gly Arg Pro Arg Ala Gly Glu Arg Asp
        210                 215                220

Asn Arg Cys Asn Arg Ala His Glu Glu Ala Gln Lys Leu Leu Pro Pro
        225                 230                235                240

Pro Pro Pro Pro Pro Pro Pro Ala Leu Pro Ser Arg Arg Pro Gly
                           245                250                255

Pro Glu Pro Cys Ala Pro Pro Ala Tyr Ala His Pro Ala Pro Ala Ser
                           260                265                270

Leu Arg Glu Cys Gly Ser Gly Arg Gly Lys Ala Ser Pro Ala Thr Gly
                           275                280                285

Arg Arg Asp Leu Ala Ile
                           290

<210> SEQ ID NO 10
<211> LENGTH: 283
<212> TYPE: PRT
<213> ORGANISM: homo sapiens
<220> FEATURE:
<221> NAME/KEY: MISC_FEATURE
<223> OTHER INFORMATION: Cx32 (NP_000157.1)

<400> SEQUENCE: 10

Met Asn Trp Thr Gly Leu Tyr Thr Leu Leu Ser Gly Val Asn Arg His
        1                   5                  10                 15

Ser Thr Ala Ile Gly Arg Val Trp Leu Ser Val Ile Phe Ile Phe Arg
                        20                 25                 30

Ile Met Val Leu Val Val Ala Ala Glu Ser Val Trp Gly Asp Glu Lys
                        35                 40                 45

Ser Ser Phe Ile Cys Asn Thr Leu Gln Pro Gly Cys Asn Ser Val Cys
                50                  55                 60
```

```
Tyr Asp Gln Phe Phe Pro Ile Ser His Val Arg Leu Trp Ser Leu Gln
 65                  70                  75                  80

Leu Ile Leu Val Ser Thr Pro Ala Leu Leu Val Ala Met His Val Ala
                 85                  90                  95

His Gln Gln His Ile Glu Lys Lys Met Leu Arg Leu Glu Gly His Gly
            100                 105                 110

Asp Pro Leu His Leu Glu Glu Val Lys Arg His Lys Val His Ile Ser
        115                 120                 125

Gly Thr Leu Trp Trp Thr Tyr Val Ile Ser Val Val Phe Arg Leu Leu
    130                 135                 140

Phe Glu Ala Val Phe Met Tyr Val Phe Tyr Leu Leu Tyr Pro Gly Tyr
145                 150                 155                 160

Ala Met Val Arg Leu Val Lys Cys Asp Val Tyr Pro Cys Pro Asn Thr
                165                 170                 175

Val Asp Cys Phe Val Ser Arg Pro Thr Glu Lys Thr Val Phe Thr Val
                180                 185                 190

Phe Met Leu Ala Ala Ser Gly Ile Cys Ile Ile Leu Asn Val Ala Glu
            195                 200                 205

Val Val Tyr Leu Ile Ile Arg Ala Cys Ala Arg Arg Ala Gln Arg Arg
        210                 215                 220

Ser Asn Pro Pro Ser Arg Lys Gly Ser Gly Phe Gly His Arg Leu Ser
225                 230                 235                 240

Pro Glu Tyr Lys Gln Asn Glu Ile Asn Lys Leu Leu Ser Glu Gln Asp
                245                 250                 255

Gly Ser Leu Lys Asp Ile Leu Arg Arg Ser Pro Gly Thr Gly Ala Gly
            260                 265                 270

Leu Ala Glu Lys Ser Asp Arg Cys Ser Ala Cys
        275                 280

<210> SEQ ID NO 11
<211> LENGTH: 321
<212> TYPE: PRT
<213> ORGANISM: homo sapiens
<220> FEATURE:
<221> NAME/KEY: MISC_FEATURE
<223> OTHER INFORMATION: Cx36 (NP_065711.1)

<400> SEQUENCE: 11

Met Gly Glu Trp Thr Ile Leu Glu Arg Leu Leu Glu Ala Ala Val Gln
 1               5                  10                  15

Gln His Ser Thr Met Ile Gly Arg Ile Leu Leu Thr Val Val Val Ile
            20                  25                  30

Phe Arg Ile Leu Ile Val Ala Ile Val Gly Glu Thr Val Tyr Asp Asp
        35                  40                  45

Glu Gln Thr Met Phe Val Cys Asn Thr Leu Gln Pro Gly Cys Asn Gln
    50                  55                  60

Ala Cys Tyr Asp Arg Ala Phe Pro Ile Ser His Ile Arg Tyr Trp Val
 65                  70                  75                  80

Phe Gln Ile Ile Met Val Cys Thr Pro Ser Leu Cys Phe Ile Thr Tyr
                 85                  90                  95

Ser Val His Gln Ser Ala Lys Gln Arg Glu Arg Arg Tyr Ser Thr Val
            100                 105                 110

Phe Leu Ala Leu Asp Arg Asp Pro Pro Glu Ser Ile Gly Gly Pro Gly
        115                 120                 125

Gly Thr Gly Gly Gly Gly Ser Gly Gly Lys Arg Glu Asp Lys Lys
    130                 135                 140
```

Leu Gln Asn Ala Ile Val Asn Gly Val Leu Gln Asn Thr Glu Asn Thr
145                 150                 155                 160

Ser Lys Glu Thr Glu Pro Asp Cys Leu Glu Val Lys Glu Leu Thr Pro
                165                 170                 175

His Pro Ser Gly Leu Arg Thr Ala Ser Lys Ser Lys Leu Arg Arg Gln
            180                 185                 190

Glu Gly Ile Ser Arg Phe Tyr Ile Ile Gln Val Val Phe Arg Asn Ala
            195                 200                 205

Leu Glu Ile Gly Phe Leu Val Gly Gln Tyr Phe Leu Tyr Gly Phe Ser
    210                 215                 220

Val Pro Gly Leu Tyr Glu Cys Asn Arg Tyr Pro Cys Ile Lys Glu Val
225                 230                 235                 240

Glu Cys Tyr Val Ser Arg Pro Thr Glu Lys Thr Val Phe Leu Val Phe
                245                 250                 255

Met Phe Ala Val Ser Gly Ile Cys Val Val Leu Asn Leu Ala Glu Leu
            260                 265                 270

Asn His Leu Gly Trp Arg Lys Ile Lys Leu Ala Val Arg Gly Ala Gln
    275                 280                 285

Ala Lys Arg Lys Ser Ile Tyr Glu Ile Arg Asn Lys Asp Leu Pro Arg
290                 295                 300

Val Ser Val Pro Asn Phe Gly Arg Thr Gln Ser Ser Asp Ser Ala Tyr
305                 310                 315                 320

Val

<210> SEQ ID NO 12
<211> LENGTH: 333
<212> TYPE: PRT
<213> ORGANISM: homo sapiens
<220> FEATURE:
<221> NAME/KEY: MISC_FEATURE
<223> OTHER INFORMATION: Cx37 (NP_002051.2)

<400> SEQUENCE: 12

Met Gly Asp Trp Gly Phe Leu Glu Lys Leu Leu Asp Gln Val Gln Glu
1               5                   10                  15

His Ser Thr Val Val Gly Lys Ile Trp Leu Thr Val Leu Phe Ile Phe
                20                  25                  30

Arg Ile Leu Ile Leu Gly Leu Ala Gly Glu Ser Val Trp Gly Asp Glu
            35                  40                  45

Gln Ser Asp Phe Glu Cys Asn Thr Ala Gln Pro Gly Cys Thr Asn Val
    50                  55                  60

Cys Tyr Asp Gln Ala Phe Pro Ile Ser His Ile Arg Tyr Trp Val Leu
65                  70                  75                  80

Gln Phe Leu Phe Val Ser Thr Pro Thr Leu Val Tyr Leu Gly His Val
                85                  90                  95

Ile Tyr Leu Ser Arg Arg Glu Glu Arg Leu Arg Gln Lys Glu Gly Glu
            100                 105                 110

Leu Arg Ala Leu Pro Ala Lys Asp Pro Gln Val Glu Arg Ala Leu Ala
    115                 120                 125

Ala Val Glu Arg Gln Met Ala Lys Ile Ser Val Ala Glu Asp Gly Arg
130                 135                 140

Leu Arg Ile Arg Gly Ala Leu Met Gly Thr Tyr Val Ala Ser Val Leu
145                 150                 155                 160

Cys Lys Ser Val Leu Glu Ala Gly Phe Leu Tyr Gly Gln Trp Arg Leu
                165                 170                 175

```
Tyr Gly Trp Thr Met Glu Pro Val Phe Val Cys Gln Arg Ala Pro Cys
                180                 185                 190
Pro Tyr Leu Val Asp Cys Phe Val Ser Arg Pro Thr Glu Lys Thr Ile
            195                 200                 205
Phe Ile Ile Phe Met Leu Val Val Gly Leu Ile Ser Leu Val Leu Asn
210                 215                 220
Leu Leu Glu Leu Val His Leu Leu Cys Arg Cys Leu Ser Arg Gly Met
225                 230                 235                 240
Arg Ala Arg Gln Gly Gln Asp Ala Pro Pro Thr Gln Gly Thr Ser Ser
                245                 250                 255
Asp Pro Tyr Thr Asp Gln Val Phe Phe Tyr Leu Pro Val Gly Gln Gly
            260                 265                 270
Pro Ser Ser Pro Pro Cys Pro Thr Tyr Asn Gly Leu Ser Ser Ser Glu
        275                 280                 285
Gln Asn Trp Ala Asn Leu Thr Thr Glu Glu Arg Leu Ala Ser Ser Arg
    290                 295                 300
Pro Pro Leu Phe Leu Asp Pro Pro Gln Asn Gly Gln Lys Pro Pro
305                 310                 315                 320
Ser Arg Pro Ser Ser Ser Ala Ser Lys Lys Gln Tyr Val
                325                 330

<210> SEQ ID NO 13
<211> LENGTH: 358
<212> TYPE: PRT
<213> ORGANISM: homo sapiens
<220> FEATURE:
<221> NAME/KEY: MISC_FEATURE
<223> OTHER INFORMATION: Cx40 (NP_005257)

<400> SEQUENCE: 13

Met Gly Asp Trp Ser Phe Leu Gly Asn Phe Leu Glu Glu Val His Lys
1               5                   10                  15
His Ser Thr Val Val Gly Lys Val Trp Leu Thr Val Leu Phe Ile Phe
                20                  25                  30
Arg Met Leu Val Leu Gly Thr Ala Ala Glu Ser Ser Trp Gly Asp Glu
            35                  40                  45
Gln Ala Asp Phe Arg Cys Asp Thr Ile Gln Pro Gly Cys Gln Asn Val
        50                  55                  60
Cys Tyr Asp Gln Ala Phe Pro Ile Ser His Ile Arg Tyr Trp Val Leu
65                  70                  75                  80
Gln Ile Ile Phe Val Ser Thr Pro Ser Leu Val Tyr Met Gly His Ala
                85                  90                  95
Met His Thr Val Arg Met Gln Glu Lys Arg Lys Leu Arg Glu Ala Glu
            100                 105                 110
Arg Ala Lys Glu Val Arg Gly Ser Gly Ser Tyr Glu Tyr Pro Val Ala
        115                 120                 125
Glu Lys Ala Glu Leu Ser Cys Trp Glu Glu Gly Asn Gly Arg Ile Ala
    130                 135                 140
Leu Gln Gly Thr Leu Leu Asn Thr Tyr Val Cys Ser Ile Leu Ile Arg
145                 150                 155                 160
Thr Thr Met Glu Val Gly Phe Ile Val Gly Gln Tyr Phe Ile Tyr Gly
                165                 170                 175
Ile Phe Leu Thr Thr Leu His Val Cys Arg Arg Ser Pro Cys Pro His
            180                 185                 190
Pro Val Asn Cys Tyr Val Ser Arg Pro Thr Glu Lys Asn Val Phe Ile
```

```
            195                 200                 205
Val Phe Met Leu Ala Val Ala Ala Leu Ser Leu Leu Ser Leu Ala
210                 215                 220

Glu Leu Tyr His Leu Gly Trp Lys Lys Ile Arg Gln Arg Phe Val Lys
225                 230                 235                 240

Pro Arg Gln His Met Ala Lys Cys Gln Leu Ser Gly Pro Ser Val Gly
                    245                 250                 255

Ile Val Gln Ser Cys Thr Pro Pro Asp Phe Asn Gln Cys Leu Glu
            260                 265                 270

Asn Gly Pro Gly Gly Lys Phe Phe Asn Pro Phe Ser Asn Asn Met Ala
                275                 280                 285

Ser Gln Gln Asn Thr Asp Asn Leu Val Thr Glu Gln Val Arg Gly Gln
290                 295                 300

Glu Gln Thr Pro Gly Glu Gly Phe Ile Gln Val Arg Tyr Gly Gln Lys
305                 310                 315                 320

Pro Glu Val Pro Asn Gly Val Ser Pro Gly His Arg Leu Pro His Gly
                    325                 330                 335

Tyr His Ser Asp Lys Arg Arg Leu Ser Lys Ala Ser Ser Lys Ala Arg
                340                 345                 350

Ser Asp Asp Leu Ser Val
                355

<210> SEQ ID NO 14
<211> LENGTH: 370
<212> TYPE: PRT
<213> ORGANISM: homo sapiens
<220> FEATURE:
<221> NAME/KEY: misc_feature
<223> OTHER INFORMATION: Cx40.1 (NP_699199.2)

<400> SEQUENCE: 14

Met Glu Gly Val Asp Leu Leu Gly Phe Leu Ile Ile Thr Leu Asn Cys
1               5                   10                  15

Asn Val Thr Met Val Gly Lys Leu Trp Phe Val Leu Thr Met Leu Leu
                20                  25                  30

Arg Met Leu Val Ile Val Leu Ala Gly Arg Pro Val Tyr Gln Asp Glu
            35                  40                  45

Gln Glu Arg Phe Val Cys Asn Thr Leu Gln Pro Gly Cys Ala Asn Val
50                  55                  60

Cys Tyr Asp Val Phe Ser Pro Val Ser His Leu Arg Phe Trp Leu Ile
65                  70                  75                  80

Gln Gly Val Cys Val Leu Leu Pro Ser Ala Val Phe Ser Val Tyr Val
                85                  90                  95

Leu His Arg Gly Ala Thr Leu Ala Ala Leu Gly Pro Arg Arg Cys Pro
            100                 105                 110

Asp Pro Arg Glu Pro Ala Ser Gly Gln Arg Arg Cys Pro Arg Pro Phe
        115                 120                 125

Gly Glu Arg Gly Gly Leu Gln Val Pro Asp Phe Ser Ala Gly Tyr Ile
130                 135                 140

Ile His Leu Leu Leu Arg Thr Leu Leu Glu Ala Ala Phe Gly Ala Leu
145                 150                 155                 160

His Tyr Phe Leu Phe Gly Phe Leu Ala Pro Lys Lys Phe Pro Cys Thr
                165                 170                 175

Arg Pro Pro Cys Thr Gly Val Val Asp Cys Tyr Val Ser Arg Pro Thr
            180                 185                 190
```

```
Glu Lys Ser Leu Leu Met Leu Phe Leu Trp Ala Val Ser Ala Leu Ser
            195                 200                 205

Phe Leu Leu Gly Leu Ala Asp Leu Val Cys Ser Leu Arg Arg Arg Met
    210                 215                 220

Arg Arg Arg Pro Gly Pro Thr Ser Pro Ser Ile Arg Lys Gln Ser
225                 230                 235                 240

Gly Ala Ser Gly His Ala Glu Gly Arg Arg Thr Asp Glu Glu Gly Gly
                245                 250                 255

Arg Glu Glu Glu Gly Ala Pro Ala Pro Gly Ala Arg Ala Gly Gly
            260                 265                 270

Glu Gly Ala Gly Ser Pro Arg Arg Thr Ser Arg Val Ser Gly His Thr
            275                 280                 285

Lys Ile Pro Asp Glu Asp Glu Ser Glu Val Thr Ser Ser Ala Ser Glu
    290                 295                 300

Lys Leu Gly Arg Gln Pro Arg Gly Arg Pro His Arg Glu Ala Ala Gln
305                 310                 315                 320

Asp Pro Arg Gly Ser Gly Ser Glu Glu Gln Pro Ser Ala Ala Pro Ser
                325                 330                 335

Arg Leu Ala Ala Pro Pro Ser Cys Ser Ser Leu Gln Pro Pro Asp Pro
            340                 345                 350

Pro Ala Ser Ser Ser Gly Ala Pro His Leu Arg Ala Arg Lys Ser Glu
            355                 360                 365

Trp Val
    370

<210> SEQ ID NO 15
<211> LENGTH: 382
<212> TYPE: PRT
<213> ORGANISM: homo sapiens
<220> FEATURE:
<221> NAME/KEY: MISC_FEATURE
<223> OTHER INFORMATION: Cx43 (NP_000156.1)

<400> SEQUENCE: 15

Met Gly Asp Trp Ser Ala Leu Gly Lys Leu Leu Asp Lys Val Gln Ala
1               5                   10                  15

Tyr Ser Thr Ala Gly Gly Lys Val Trp Leu Ser Val Leu Phe Ile Phe
            20                  25                  30

Arg Ile Leu Leu Leu Gly Thr Ala Val Glu Ser Ala Trp Gly Asp Glu
        35                  40                  45

Gln Ser Ala Phe Arg Cys Asn Thr Gln Gln Pro Gly Cys Glu Asn Val
    50                  55                  60

Cys Tyr Asp Lys Ser Phe Pro Ile Ser His Val Arg Phe Trp Val Leu
65                  70                  75                  80

Gln Ile Ile Phe Val Ser Val Pro Thr Leu Leu Tyr Leu Ala His Val
                85                  90                  95

Phe Tyr Val Met Arg Lys Glu Glu Lys Leu Asn Lys Lys Glu Glu Glu
            100                 105                 110

Leu Lys Val Ala Gln Thr Asp Gly Val Asn Val Asp Met His Leu Lys
        115                 120                 125

Gln Ile Glu Ile Lys Lys Phe Lys Tyr Gly Ile Glu Glu His Gly Lys
    130                 135                 140

Val Lys Met Arg Gly Gly Leu Leu Arg Thr Tyr Ile Ile Ser Ile Leu
145                 150                 155                 160

Phe Lys Ser Ile Phe Glu Val Ala Phe Leu Leu Ile Gln Trp Tyr Ile
                165                 170                 175
```

```
Tyr Gly Phe Ser Leu Ser Ala Val Tyr Thr Cys Lys Arg Asp Pro Cys
            180                 185                 190

Pro His Gln Val Asp Cys Phe Leu Ser Arg Pro Thr Glu Lys Thr Ile
            195                 200                 205

Phe Ile Ile Phe Met Leu Val Val Ser Leu Val Ser Leu Ala Leu Asn
210                 215                 220

Ile Ile Glu Leu Phe Tyr Val Phe Phe Lys Gly Val Lys Asp Arg Val
225                 230                 235                 240

Lys Gly Lys Ser Asp Pro Tyr His Ala Thr Ser Gly Ala Leu Ser Pro
            245                 250                 255

Ala Lys Asp Cys Gly Ser Gln Lys Tyr Ala Tyr Phe Asn Gly Cys Ser
            260                 265                 270

Ser Pro Thr Ala Pro Leu Ser Pro Met Ser Pro Pro Gly Tyr Lys Leu
            275                 280                 285

Val Thr Gly Asp Arg Asn Asn Ser Ser Cys Arg Asn Tyr Asn Lys Gln
            290                 295                 300

Ala Ser Glu Gln Asn Trp Ala Asn Tyr Ser Ala Glu Gln Asn Arg Met
305                 310                 315                 320

Gly Gln Ala Gly Ser Thr Ile Ser Asn Ser His Ala Gln Pro Phe Asp
            325                 330                 335

Phe Pro Asp Asp Asn Gln Asn Ser Lys Lys Leu Ala Ala Gly His Glu
            340                 345                 350

Leu Gln Pro Leu Ala Ile Val Asp Gln Arg Pro Ser Ser Arg Ala Ser
            355                 360                 365

Ser Arg Ala Ser Ser Arg Pro Arg Pro Asp Asp Leu Glu Ile
            370                 375                 380

<210> SEQ ID NO 16
<211> LENGTH: 396
<212> TYPE: PRT
<213> ORGANISM: homo sapiens
<220> FEATURE:
<221> NAME/KEY: MISC_FEATURE
<223> OTHER INFORMATION: Cx45 (NP_001073852.1)

<400> SEQUENCE: 16

Met Ser Trp Ser Phe Leu Thr Arg Leu Leu Glu Glu Ile His Asn His
1               5                   10                  15

Ser Thr Phe Val Gly Lys Ile Trp Leu Thr Val Leu Ile Val Phe Arg
            20                  25                  30

Ile Val Leu Thr Ala Val Gly Gly Glu Ser Ile Tyr Tyr Asp Glu Gln
            35                  40                  45

Ser Lys Phe Val Cys Asn Thr Glu Gln Pro Gly Cys Glu Asn Val Cys
        50                  55                  60

Tyr Asp Ala Phe Ala Pro Leu Ser His Val Arg Phe Trp Val Phe Gln
65                  70                  75                  80

Ile Ile Leu Val Ala Thr Pro Ser Val Met Tyr Leu Gly Tyr Ala Ile
                85                  90                  95

His Lys Ile Ala Lys Met Glu His Gly Glu Ala Asp Lys Lys Ala Ala
            100                 105                 110

Arg Ser Lys Pro Tyr Ala Met Arg Trp Lys Gln His Arg Ala Leu Glu
            115                 120                 125

Glu Thr Glu Glu Asp Asn Glu Glu Asp Pro Met Met Tyr Pro Glu Met
            130                 135                 140

Glu Leu Glu Ser Asp Lys Glu Asn Lys Glu Gln Ser Gln Pro Lys Pro
```

```
                145                 150                 155                 160
        Lys His Asp Gly Arg Arg Ile Arg Glu Asp Gly Leu Met Lys Ile
                            165                 170                 175

Tyr Val Leu Gln Leu Leu Ala Arg Thr Val Phe Glu Val Gly Phe Leu
                            180                 185                 190

Ile Gly Gln Tyr Phe Leu Tyr Gly Phe Gln Val His Pro Phe Tyr Val
                            195                 200                 205

Cys Ser Arg Leu Pro Cys Pro His Lys Ile Asp Cys Phe Ile Ser Arg
            210                 215                 220

Pro Thr Glu Lys Thr Ile Phe Leu Leu Ile Met Tyr Gly Val Thr Gly
        225                 230                 235                 240

Leu Cys Leu Leu Leu Asn Ile Trp Glu Met Leu His Leu Gly Phe Gly
                            245                 250                 255

Thr Ile Arg Asp Ser Leu Asn Ser Lys Arg Arg Glu Leu Glu Asp Pro
                        260                 265                 270

Gly Ala Tyr Asn Tyr Pro Phe Thr Trp Asn Thr Pro Ser Ala Pro Pro
                        275                 280                 285

Gly Tyr Asn Ile Ala Val Lys Pro Asp Gln Ile Gln Tyr Thr Glu Leu
                        290                 295                 300

Ser Asn Ala Lys Ile Ala Tyr Lys Gln Asn Lys Ala Asn Thr Ala Gln
        305                 310                 315                 320

Glu Gln Gln Tyr Gly Ser His Glu Glu Asn Leu Pro Ala Asp Leu Glu
                        325                 330                 335

Ala Leu Gln Arg Glu Ile Arg Met Ala Gln Glu Arg Leu Asp Leu Ala
                        340                 345                 350

Val Gln Ala Tyr Ser His Gln Asn Asn Pro His Gly Pro Arg Glu Lys
                    355                 360                 365

Lys Ala Lys Val Gly Ser Lys Ala Gly Ser Asn Lys Ser Thr Ala Ser
                    370                 375                 380

Ser Lys Ser Gly Asp Gly Lys Thr Ser Val Trp Ile
        385                 390                 395

<210> SEQ ID NO 17
<211> LENGTH: 435
<212> TYPE: PRT
<213> ORGANISM: homo sapiens
<220> FEATURE:
<221> NAME/KEY: MISC_FEATURE
<223> OTHER INFORMATION: Cx46 (NP_068773.2)

<400> SEQUENCE: 17

Met Gly Asp Trp Ser Phe Leu Gly Arg Leu Leu Glu Asn Ala Gln Glu
        1               5                   10                  15

His Ser Thr Val Ile Gly Lys Val Trp Leu Thr Val Leu Phe Ile Phe
                        20                  25                  30

Arg Ile Leu Val Leu Gly Ala Ala Glu Asp Val Trp Gly Asp Glu
                    35                  40                  45

Gln Ser Asp Phe Thr Cys Asn Thr Gln Gln Pro Gly Cys Glu Asn Val
                50                  55                  60

Cys Tyr Asp Arg Ala Phe Pro Ile Ser His Ile Arg Phe Trp Ala Leu
        65                  70                  75                  80

Gln Ile Ile Phe Val Ser Thr Pro Thr Leu Ile Tyr Leu Gly His Val
                        85                  90                  95

Leu His Ile Val Arg Met Glu Glu Lys Lys Glu Arg Glu Glu Glu
                        100                 105                 110
```

```
Glu Gln Leu Lys Arg Glu Ser Pro Ser Pro Lys Glu Pro Gln Asp
            115                 120                 125

Asn Pro Ser Ser Arg Asp Asp Arg Gly Arg Val Arg Met Ala Gly Ala
130                 135                 140

Leu Leu Arg Thr Tyr Val Phe Asn Ile Ile Phe Lys Thr Leu Phe Glu
145                 150                 155                 160

Val Gly Phe Ile Ala Gly Gln Tyr Phe Leu Tyr Gly Phe Glu Leu Lys
                165                 170                 175

Pro Leu Tyr Arg Cys Asp Arg Trp Pro Cys Pro Asn Thr Val Asp Cys
            180                 185                 190

Phe Ile Ser Arg Pro Thr Glu Lys Thr Ile Phe Ile Ile Phe Met Leu
            195                 200                 205

Ala Val Ala Cys Ala Ser Leu Leu Leu Asn Met Leu Glu Ile Tyr His
        210                 215                 220

Leu Gly Trp Lys Lys Leu Lys Gln Gly Val Thr Ser Arg Leu Gly Pro
225                 230                 235                 240

Asp Ala Ser Glu Ala Pro Leu Gly Thr Ala Asp Pro Pro Leu Pro
                245                 250                 255

Pro Ser Ser Arg Pro Pro Ala Val Ala Ile Gly Phe Pro Pro Tyr Tyr
            260                 265                 270

Ala His Thr Ala Ala Pro Leu Gly Gln Ala Arg Ala Val Gly Tyr Pro
        275                 280                 285

Gly Ala Pro Pro Ala Ala Asp Phe Lys Leu Leu Ala Leu Thr Glu
290                 295                 300

Ala Arg Gly Lys Gly Gln Ser Ala Lys Leu Tyr Asn Gly His His His
305                 310                 315                 320

Leu Leu Met Thr Glu Gln Asn Trp Ala Asn Gln Ala Ala Glu Arg Gln
                325                 330                 335

Pro Pro Ala Leu Lys Ala Tyr Pro Ala Ala Ser Thr Pro Ala Ala Pro
            340                 345                 350

Ser Pro Val Gly Ser Ser Pro Pro Leu Ala His Glu Ala Glu Ala
        355                 360                 365

Gly Ala Ala Pro Leu Leu Leu Asp Gly Ser Gly Ser Ser Leu Glu Gly
370                 375                 380

Ser Ala Leu Ala Gly Thr Pro Glu Glu Glu Gln Ala Val Thr Thr
385                 390                 395                 400

Ala Ala Gln Met His Gln Pro Pro Leu Pro Leu Gly Asp Pro Gly Arg
                405                 410                 415

Ala Ser Lys Ala Ser Arg Ala Ser Gly Arg Ala Arg Pro Glu Asp
            420                 425                 430

Leu Ala Ile
        435

<210> SEQ ID NO 18
<211> LENGTH: 439
<212> TYPE: PRT
<213> ORGANISM: homo sapiens
<220> FEATURE:
<221> NAME/KEY: MISC_FEATURE
<223> OTHER INFORMATION: Cx47 (NP_065168.2)

<400> SEQUENCE: 18

Met Thr Asn Met Ser Trp Ser Phe Leu Thr Arg Leu Leu Glu Glu Ile
1               5                   10                  15

His Asn His Ser Thr Phe Val Gly Lys Val Trp Leu Thr Val Leu Val
                20                  25                  30
```

-continued

```
Val Phe Arg Ile Val Leu Thr Ala Val Gly Gly Glu Ala Ile Tyr Ser
         35                  40                  45

Asp Glu Gln Ala Lys Phe Thr Cys Asn Thr Arg Gln Pro Gly Cys Asp
 50                  55                  60

Asn Val Cys Tyr Asp Ala Phe Ala Pro Leu Ser His Val Arg Phe Trp
 65                  70                  75                  80

Val Phe Gln Ile Val Ile Ser Thr Pro Ser Val Met Tyr Leu Gly
                     85                  90                  95

Tyr Ala Val His Arg Leu Ala Arg Ala Ser Glu Gln Glu Arg Arg Arg
                    100                 105                 110

Ala Leu Arg Arg Pro Gly Pro Arg Ala Pro Arg Ala His Leu
                    115                 120                 125

Pro Pro Pro His Ala Gly Trp Pro Glu Pro Ala Asp Leu Gly Glu Glu
                    130                 135                 140

Glu Pro Met Leu Gly Leu Gly Glu Glu Glu Glu Glu Thr Gly
145                 150                 155                 160

Ala Ala Glu Gly Ala Gly Glu Ala Glu Ala Gly Ala Glu Glu
                    165                 170                 175

Ala Cys Thr Lys Ala Val Gly Ala Asp Gly Lys Ala Ala Gly Thr Pro
                    180                 185                 190

Gly Pro Thr Gly Gln His Asp Gly Arg Arg Ile Gln Arg Glu Gly
                    195                 200                 205

Leu Met Arg Val Tyr Val Ala Gln Leu Val Arg Ala Ala Phe Glu
    210                 215                 220

Val Ala Phe Leu Val Gly Gln Tyr Leu Leu Tyr Gly Phe Glu Val Arg
225                 230                 235                 240

Pro Phe Phe Pro Cys Ser Arg Gln Pro Cys Pro His Val Val Asp Cys
                    245                 250                 255

Phe Val Ser Arg Pro Thr Glu Lys Thr Val Phe Leu Leu Val Met Tyr
                    260                 265                 270

Val Val Ser Cys Leu Cys Leu Leu Asn Leu Cys Glu Met Ala His
                    275                 280                 285

Leu Gly Leu Gly Ser Ala Gln Asp Ala Val Arg Gly Arg Arg Gly Pro
    290                 295                 300

Pro Ala Ser Ala Pro Ala Pro Arg Pro Pro Cys Ala Phe
305                 310                 315                 320

Pro Ala Ala Ala Gly Leu Ala Cys Pro Pro Asp Tyr Ser Leu Val
                    325                 330                 335

Val Arg Ala Ala Glu Arg Ala Arg Ala His Asp Gln Asn Leu Ala Asn
                    340                 345                 350

Leu Ala Leu Gln Ala Leu Arg Asp Gly Ala Ala Gly Asp Arg Asp
                    355                 360                 365

Arg Asp Ser Ser Pro Cys Val Gly Leu Pro Ala Ala Ser Arg Gly Pro
    370                 375                 380

Pro Arg Ala Gly Ala Pro Ala Ser Arg Thr Gly Ser Ala Thr Ser Ala
385                 390                 395                 400

Gly Thr Val Gly Glu Gln Gly Arg Pro Gly Thr His Glu Arg Pro Gly
                    405                 410                 415

Ala Lys Pro Arg Ala Gly Ser Glu Lys Gly Ser Ala Ser Ser Arg Asp
                    420                 425                 430

Gly Lys Thr Thr Val Trp Ile
                    435
```

<210> SEQ ID NO 19
<211> LENGTH: 433
<212> TYPE: PRT
<213> ORGANISM: homo sapiens
<220> FEATURE:
<221> NAME/KEY: MISC_FEATURE
<223> OTHER INFORMATION: Cx50 (NP_005258.2)

<400> SEQUENCE: 19

```
Met Gly Asp Trp Ser Phe Leu Gly Asn Ile Leu Glu Glu Val Asn Glu
1               5                   10                  15

His Ser Thr Val Ile Gly Arg Val Trp Leu Thr Val Leu Phe Ile Phe
            20                  25                  30

Arg Ile Leu Ile Leu Gly Thr Ala Ala Glu Phe Val Trp Gly Asp Glu
        35                  40                  45

Gln Ser Asp Phe Val Cys Asn Thr Gln Gln Pro Gly Cys Glu Asn Val
    50                  55                  60

Cys Tyr Asp Glu Ala Phe Pro Ile Ser His Ile Arg Leu Trp Val Leu
65                  70                  75                  80

Gln Ile Ile Phe Val Ser Thr Pro Ser Leu Met Tyr Val Gly His Ala
                85                  90                  95

Val His Tyr Val Arg Met Glu Glu Lys Arg Lys Ser Arg Glu Ala Glu
            100                 105                 110

Glu Leu Gly Gln Gln Ala Gly Thr Asn Gly Gly Pro Asp Gln Gly Ser
        115                 120                 125

Val Lys Lys Ser Ser Gly Ser Lys Gly Thr Lys Phe Arg Leu Glu
    130                 135                 140

Gly Thr Leu Leu Arg Thr Tyr Ile Cys His Ile Ile Phe Lys Thr Leu
145                 150                 155                 160

Phe Glu Val Gly Phe Ile Val Gly His Tyr Phe Leu Tyr Gly Phe Arg
                165                 170                 175

Ile Leu Pro Leu Tyr Arg Cys Ser Arg Trp Pro Cys Pro Asn Val Val
            180                 185                 190

Asp Cys Phe Val Ser Arg Pro Thr Glu Lys Thr Ile Phe Ile Leu Phe
        195                 200                 205

Met Leu Ser Val Ala Ser Val Ser Leu Phe Leu Asn Val Met Glu Leu
    210                 215                 220

Gly His Leu Gly Leu Lys Gly Ile Arg Ser Ala Leu Lys Arg Pro Val
225                 230                 235                 240

Glu Gln Pro Leu Gly Glu Ile Pro Glu Lys Ser Leu His Ser Ile Ala
                245                 250                 255

Val Ser Ser Ile Gln Lys Ala Lys Gly Tyr Gln Leu Leu Glu Glu Glu
            260                 265                 270

Lys Ile Val Ser His Tyr Phe Pro Leu Thr Glu Val Gly Met Val Glu
        275                 280                 285

Thr Ser Pro Leu Pro Ala Lys Pro Phe Asn Gln Phe Glu Glu Lys Ile
    290                 295                 300

Ser Thr Gly Pro Leu Gly Asp Leu Ser Arg Gly Tyr Gln Glu Thr Leu
305                 310                 315                 320

Pro Ser Tyr Ala Gln Val Gly Ala Gln Glu Val Glu Gly Glu Gly Pro
                325                 330                 335

Pro Ala Glu Glu Gly Ala Glu Pro Glu Val Gly Glu Lys Lys Glu Glu
            340                 345                 350

Ala Glu Arg Leu Thr Thr Glu Glu Gln Glu Lys Val Ala Val Pro Glu
        355                 360                 365
```

-continued

Gly Glu Lys Val Glu Thr Pro Gly Val Asp Lys Gly Glu Lys Glu
        370                 375                 380

Glu Pro Gln Ser Glu Lys Val Ser Lys Gln Gly Leu Pro Ala Glu Lys
385                 390                 395                 400

Thr Pro Ser Leu Cys Pro Glu Leu Thr Thr Asp Asp Ala Arg Pro Leu
                405                 410                 415

Ser Arg Leu Ser Lys Ala Ser Ser Arg Ala Arg Ser Asp Asp Leu Thr
            420                 425                 430

Val

<210> SEQ ID NO 20
<211> LENGTH: 515
<212> TYPE: PRT
<213> ORGANISM: homo sapiens
<220> FEATURE:
<221> NAME/KEY: MISC_FEATURE
<223> OTHER INFORMATION: Cx59 (NP_110399.2)

<400> SEQUENCE: 20

Met Gly Asp Trp Asn Leu Leu Gly Asp Thr Leu Glu Glu Val His Ile
1               5                   10                  15

His Ser Thr Met Ile Gly Lys Ile Trp Leu Thr Ile Leu Phe Ile Phe
            20                  25                  30

Arg Met Leu Val Leu Gly Val Ala Ala Glu Asp Val Trp Asn Asp Glu
        35                  40                  45

Gln Ser Gly Phe Ile Cys Asn Thr Glu Gln Pro Gly Cys Arg Asn Val
    50                  55                  60

Cys Tyr Asp Gln Ala Phe Pro Ile Ser Leu Ile Arg Tyr Trp Val Leu
65                  70                  75                  80

Gln Val Ile Phe Val Ser Ser Pro Ser Leu Val Tyr Met Gly His Ala
                85                  90                  95

Leu Tyr Arg Leu Arg Val Leu Glu Glu Glu Arg Gln Arg Met Lys Ala
            100                 105                 110

Gln Leu Arg Val Glu Leu Glu Glu Val Glu Phe Glu Met Pro Arg Asp
        115                 120                 125

Arg Arg Arg Leu Glu Gln Glu Leu Cys Gln Leu Glu Lys Arg Lys Leu
    130                 135                 140

Asn Lys Ala Pro Leu Arg Gly Thr Leu Leu Cys Thr Tyr Val Ile His
145                 150                 155                 160

Ile Phe Thr Arg Ser Val Val Glu Val Gly Phe Met Ile Gly Gln Tyr
                165                 170                 175

Leu Leu Tyr Gly Phe His Leu Glu Pro Leu Phe Lys Cys His Gly His
            180                 185                 190

Pro Cys Pro Asn Ile Ile Asp Cys Phe Val Ser Arg Pro Thr Glu Lys
        195                 200                 205

Thr Ile Phe Leu Leu Phe Met Gln Ser Ile Ala Thr Ile Ser Leu Phe
    210                 215                 220

Leu Asn Ile Leu Glu Ile Phe His Leu Gly Phe Lys Lys Ile Lys Arg
225                 230                 235                 240

Gly Leu Trp Gly Lys Tyr Lys Leu Lys Lys Glu His Asn Glu Phe His
                245                 250                 255

Ala Asn Lys Ala Lys Gln Asn Val Ala Lys Tyr Gln Ser Thr Ser Ala
            260                 265                 270

Asn Ser Leu Lys Arg Leu Pro Ser Ala Pro Asp Tyr Asn Leu Leu Val
        275                 280                 285

```
Glu Lys Gln Thr His Thr Ala Val Tyr Pro Ser Leu Asn Ser Ser Ser
    290                 295                 300

Val Phe Gln Pro Asn Pro Asp Asn His Ser Val Asn Asp Glu Lys Cys
305                 310                 315                 320

Ile Leu Asp Glu Gln Glu Thr Val Leu Ser Asn Glu Ile Ser Thr Leu
                325                 330                 335

Ser Thr Ser Cys Ser His Phe Gln His Ile Ser Ser Asn Asn Asn Lys
            340                 345                 350

Asp Thr His Lys Ile Phe Gly Lys Glu Leu Asn Gly Asn Gln Leu Met
        355                 360                 365

Glu Lys Arg Glu Thr Glu Gly Lys Asp Ser Lys Arg Asn Tyr Tyr Ser
    370                 375                 380

Arg Gly His Arg Ser Ile Pro Gly Val Ala Ile Asp Gly Glu Asn Asn
385                 390                 395                 400

Met Arg Gln Ser Pro Gln Thr Val Phe Ser Leu Pro Ala Asn Cys Asp
                405                 410                 415

Trp Lys Pro Arg Trp Leu Arg Ala Thr Trp Gly Ser Ser Thr Glu His
            420                 425                 430

Glu Asn Arg Gly Ser Pro Pro Lys Gly Asn Leu Lys Gly Gln Phe Arg
        435                 440                 445

Lys Gly Thr Val Arg Thr Leu Pro Pro Ser Gln Gly Asp Ser Gln Ser
    450                 455                 460

Leu Asp Ile Pro Asn Thr Ala Asp Ser Leu Gly Gly Leu Ser Phe Glu
465                 470                 475                 480

Pro Gly Leu Val Arg Thr Cys Asn Asn Pro Val Cys Pro Asn His
                485                 490                 495

Val Val Ser Leu Thr Asn Asn Leu Ile Gly Arg Arg Val Pro Thr Asp
            500                 505                 510

Leu Gln Ile
        515

<210> SEQ ID NO 21
<211> LENGTH: 543
<212> TYPE: PRT
<213> ORGANISM: homo sapiens
<220> FEATURE:
<221> NAME/KEY: MISC_FEATURE
<223> OTHER INFORMATION: Cx62 (NP_115991.1)

<400> SEQUENCE: 21

Met Gly Asp Trp Asn Leu Leu Gly Gly Ile Leu Glu Glu Val His Ser
1               5                   10                  15

His Ser Thr Ile Val Gly Lys Ile Trp Leu Thr Ile Leu Phe Ile Phe
            20                  25                  30

Arg Met Leu Val Leu Arg Val Ala Ala Glu Asp Val Trp Asp Asp Glu
        35                  40                  45

Gln Ser Ala Phe Ala Cys Asn Thr Arg Gln Pro Gly Cys Asn Asn Ile
    50                  55                  60

Cys Tyr Asp Asp Ala Phe Pro Ile Ser Leu Ile Arg Phe Trp Val Leu
65                  70                  75                  80

Gln Ile Ile Phe Val Ser Ser Pro Ser Leu Val Tyr Met Gly His Ala
                85                  90                  95

Leu Tyr Arg Leu Arg Ala Phe Glu Lys Asp Arg Gln Arg Lys Lys Ser
            100                 105                 110

His Leu Arg Ala Gln Met Glu Asn Pro Asp Leu Asp Leu Glu Glu Gln
```

```
            115                 120                 125
Gln Arg Ile Asp Arg Glu Leu Arg Arg Leu Glu Glu Gln Lys Arg Ile
            130                 135                 140

His Lys Val Pro Leu Lys Gly Cys Leu Leu Arg Thr Tyr Val Leu His
145                 150                 155                 160

Ile Leu Thr Arg Ser Val Leu Glu Val Gly Phe Met Ile Gly Gln Tyr
                165                 170                 175

Ile Leu Tyr Gly Phe Gln Met His Pro Leu Tyr Lys Cys Thr Gln Pro
            180                 185                 190

Pro Cys Pro Asn Ala Val Asp Cys Phe Val Ser Arg Pro Thr Glu Lys
                195                 200                 205

Thr Ile Phe Met Leu Phe Met His Ser Ile Ala Ala Ile Ser Leu Leu
210                 215                 220

Leu Asn Ile Leu Glu Ile Phe His Leu Gly Ile Arg Lys Ile Met Arg
225                 230                 235                 240

Thr Leu Tyr Lys Lys Ser Ser Ser Glu Gly Ile Glu Asp Glu Thr Gly
                245                 250                 255

Pro Pro Phe His Leu Lys Lys Tyr Ser Val Ala Gln Gln Cys Met Ile
            260                 265                 270

Cys Ser Ser Leu Pro Glu Arg Ile Ser Pro Leu Gln Ala Asn Asn Gln
        275                 280                 285

Gln Gln Val Ile Arg Val Asn Val Pro Lys Ser Lys Thr Met Trp Gln
        290                 295                 300

Ile Pro Gln Pro Arg Gln Leu Glu Val Asp Pro Ser Asn Gly Lys Lys
305                 310                 315                 320

Asp Trp Ser Glu Lys Asp Gln His Ser Gly Gln Leu His Val His Ser
                325                 330                 335

Pro Cys Pro Trp Ala Gly Ser Ala Gly Asn Gln His Leu Gly Gln Gln
            340                 345                 350

Ser Asp His Ser Ser Phe Gly Leu Gln Asn Thr Met Ser Gln Ser Trp
            355                 360                 365

Leu Gly Thr Thr Thr Ala Pro Arg Asn Cys Pro Ser Phe Ala Val Gly
        370                 375                 380

Thr Trp Glu Gln Ser Gln Asp Pro Glu Pro Ser Gly Glu Pro Leu Thr
385                 390                 395                 400

Asp Leu His Ser His Cys Arg Asp Ser Glu Gly Ser Met Arg Glu Ser
                405                 410                 415

Gly Val Trp Ile Asp Arg Ser Arg Pro Gly Ser Arg Lys Ala Ser Phe
            420                 425                 430

Leu Ser Arg Leu Leu Ser Glu Lys Arg His Leu His Ser Asp Ser Gly
        435                 440                 445

Ser Ser Gly Ser Arg Asn Ser Ser Cys Leu Asp Phe Pro His Trp Glu
        450                 455                 460

Asn Ser Pro Ser Pro Leu Pro Ser Val Thr Gly His Arg Thr Ser Met
465                 470                 475                 480

Val Arg Gln Ala Ala Leu Pro Ile Met Glu Leu Ser Gln Glu Leu Phe
                485                 490                 495

His Ser Gly Cys Phe Leu Phe Pro Phe Leu Pro Gly Val Cys Met
            500                 505                 510

Tyr Val Cys Val Asp Arg Glu Ala Asp Gly Gly Gly Asp Tyr Leu Trp
            515                 520                 525
```

```
Arg Asp Lys Ile Ile His Ser Ile His Ser Val Lys Phe Asn Ser
     530             535             540
```

USE OF FLECAINIDE AS AN ANTI-CONNEXIN AGENT AND METHOD FOR POTENTIATING THE EFFECTS OF A PSYCHOTROPIC DRUG

CROSS REFERENCE TO RELATED APPLICATIONS

This application is a divisional application which claims priority to U.S. patent application Ser. No. 15/667,999, filed on Aug. 3, 2017, which is a continuation application which claims priority to U.S. patent application Ser. No. 14/907,221, filed on Jan. 22, 2016, which is a National Stage Application under 35 U.S.C. 371 of co-pending PCT application PCT/EP2014/065975 designating the United States and filed Jul. 24, 2014; which claims the benefit of EP application No. 13306074.9, filed Jul. 24, 2013 each of which are hereby incorporated by reference in their entireties.

SUMMARY OF THE INVENTION

The present invention relates to the use of flecainide as an anti-connexin agent. This anti-connexin agent is advantageously used to potentiate the therapeutic effect of various psychotropic drugs. More specifically, the invention provides a combination product containing flecainide and modafinil.

BACKGROUND OF THE INVENTION

Gap junctions are involved in intercellular communication, which is important for maintaining tissue and organ homeostasis. Gap junctions connect the cell cytoplasm, enabling the exchange of ions ($Ca^+$ and $K^+$), second messengers (AMPc, GMPc, IP3), several small metabolites (glucose) and ensuring electrical and metabolic coupling between the cells. The gap junctions are junctions with a selective permeability, formed by protein channels contained in the plasma membrane, and formed by connexin hexamers. Connexin hexamers might as well form hemichannel, linked the intracellular space to extracellular one.

Connexins are integral proteins of the plasma membrane, which are synthesized by practically every cell type, regardless of the position of a multicellular organism in the phylogenesis of the animal world. In vertebrates, occasional cells not producing connexins are adult striated muscle cells, spermatozoids and circulating blood cells. Unlike numerous membrane proteins, connexins have a short half-life (between 3 and 6 hours), are not glycosylated and do not have an enzymatic activity. At present, at least thirteen distinct connexins have been identified in mammals; corresponding, in humans, to 21 isoforms. In practice, various types of connexins can be present in a plurality of tissues, and most of the cells synthesize a plurality of connexins. Before reaching the cell membrane, the connexins assemble in groups of six molecules to form hollow tubular structures called connexons, which join the plasma membrane by means of Golgi vesicles. When cell contact is established, the connexons of a cell align end-to-end with those of the neighboring cell, establishing a continuous hydrophilic channel around 10 nm long. This junctional channel establishes direct contact between the cytoplasms of the two cells in contact, over the intercellular space.

Connexins are involved in a huge number of physiological processes, and several applications of connexin blocking agents (also called hereafter "connexin blocking agents" or "anti-connexin agents") have been described.

For example, anti-connexin agents have been proposed for treating and/or preventing the following conditions:
cancers (WO2006/134494 and WO2006/049157),
some cardiovascular diseases (WO2006/134494),
wounds (WO2006/134494 and WO2009/097077),
pain (WO2009/148613),
migraines (Durham and Garrett, 2009),
epilepsy (Juszczak and Swiergiel, 2009),
neurological conditions (WO2006/134494) and neurodegenerative diseases (Takeuchi et al. 2011),
ischemia (Davidson et al, 2013),
drug-induced liver injury (Patel et al, 2012)
infectious diseases (WO2011/067607),
cytotoxicity induced by chemotherapeutic agents (Tong X. et al, 2013) and
inflammatory disorders (WO2006/134494).

Furthermore, the present inventors previously described that anti-connexin agents are able to potentiate the therapeutic effects of psychotropic drugs (WO 2010/029131). In particular, they described that administration of anti-connexin agents such as meclofenamic acid (MFA) increases the therapeutic effects of various psychotropic molecules, enabling to reduce the active doses and thus the undesirable effects of these psychotropic molecules. These synergistic effects have been observed with a wide range of psychotropic molecules (clozapine, paroxetine, modafinil, diazepam, venlafaxine, escitalopram, bupropion and sertraline).

Identifying new anti-connexin agents is therefore of primary importance to highlight new therapeutic tools aiming to treat various diseases and disorders, in particular in combination with psychotropic drugs.

In this context, the inventors have now demonstrated that the well-known antiarrhythmic agent flecainide, has a broad anti-connexin activity. This is a very surprising result, since flecainide had been described so far to interfere with sodium channels, in particular on heart muscle cells, and these channels are not related with brain gap junctions. Moreover, flecainide had been shown not to influence junctional resistance of cardiac myocyte cell pairs (Daleau et al, 1998).

DETAILED DESCRIPTION OF THE INVENTION

In the context of the invention, "flecainide" designates a compound of formula N-(piperidin-2-ylmethyl)-2,5-bis(2,2,2-trifluoroethoxy) benzamide. As used herein, this term designates any form of this compound, such as a salt thereof. Preferably, said salt is the flecainide acetate. This term may also encompass the flecainide precursors which can be metabolized in the human body and/or its derivatives (for example, chemical derivatives resulting from one or several halogen substitutions and/or from addition of protective groups).

Figure 5A:
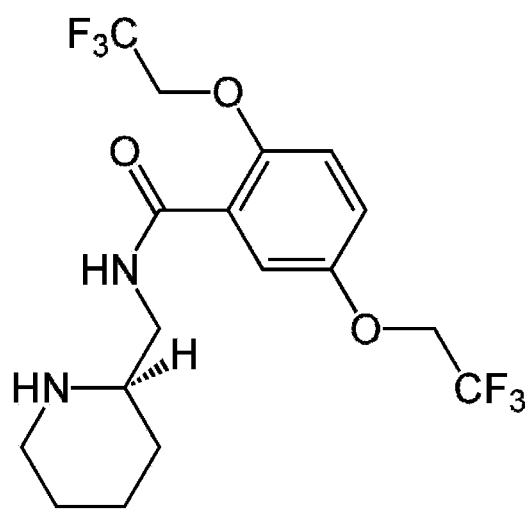
Figure 5B:
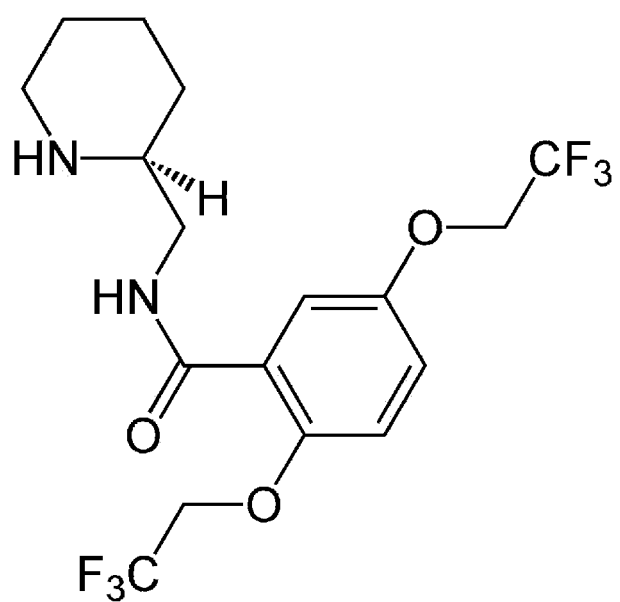

As disclosed on FIGS. 5A and 5B, flecainide possesses a chiral center implying the existence of an R and S enantiomers (S-(+)-flecainide and R-(−)-flecainide). FIGS. 5A-5B show the formulas of R-flecainide (FIG. 5A, (R)—N-(piperidin-2-ylmethyl)-2,5-bis(2,2,2-trifluoroethoxy)benzamide) and S-flecainide (FIG. 5B, (S)—N-(piperidin-2-ylmethyl)-2,5-bis(2,2,2-trifluoroethoxy)benzamide).

As used herein, the term "flecainide" designates the racemate form of N-(piperidin-2-ylmethyl)-2,5-bis(2,2,2-trifluoroethoxy) benzamide, as well as the R and S enantiomers thereof ((R)—N-(piperidin-2-ylmethyl)-2,5-bis (2,2,2-trifluoroethoxy)benzamide and (S)—N-(piperidin-2- ylmethyl)-2,5-bis(2,2,2-trifluoroethoxy)benzamide, respectively). In a preferred embodiment of the invention, the R enantiomer of flecainide ((R)—N-(piperidin-2-ylmethyl)-2, 5-bis(2,2,2-trifluoroethoxy)benzamide) will be used.

Flecainide is currently administered as a racemate (Kroemer et al, 1989; Lie et al, 1989). The pharmacokinetic parameters of the two enantiomers of flecainide have been largely described, after administration in human and rodents, as described below:

In 1989, Kroemer et al. published a study in 13 patients receiving long-term oral flecainide therapy. S-flecainide and R-flecainide plasma levels were determined, and plasma concentrations of R-flecainide were significantly higher than those of the S-flecainide enantiomer (R/S ratio=1.10), suggesting that the flecainide drug undergoes modest enantioselective disposition [Kroemer et al, 1989].

In 1989, Gross et al. compared the disposition of the two enantiomers in two human populations: extensive (EM) and five poor (PM) metabolizers of sparteine/debrisoquine after administration of 50 mg of racemic flecainide acetate [Gross et al, 1989]. Gross et al. presented data indicating that the half-life of R-flecainide (12.9 h) was longer (P<0.03) than that of S-flecainide (9.8 h). The renal clearance of the two enantiomers was, however, comparable and similar to that observed in the EM subjects. The urinary recovery of R-flecainide (15.6±3.7 mg) was greater (P<0.03) than that of the S-enantiomer (12.0±3.7 mg). The enantioselective disposition observed in PMs is therefore due to greater impairment in the metabolism of R-flecainide than S-flecainide.

In 1991, Alessi-Severini et al. summarized key findings on pharmacokinetics and concluded that there was no evidence of enantioselective disposition of flecainide in human [Alessi-Severini et al., 1991], citing three reports on stereoselective therapeutic monitoring, which found R/S ratio ranges of 0.67-1.39 (mean 1.03±0.16), 0.75-1.44 (mean 1.04), and 0.89-1.32 (mean 1.10±0.13), and that Gross et al. 1989 study was not relevant on the total population.

In 1998, Hanada et al. demonstrated an absence of enantioselective distribution of the two enantiomers of flecainide in several tissue, after intravenous administration of flecainide racemate in rats [Hanada et al, 1998].

As reviewed in [Mehvar et al, 2002], it appears that the renal clearances of the enantiomers of flecainide are not stereoselective in both healthy volunteers and patients.

Literature is thus globally coherent on the absence of stereoselective effects of flecainide on pharmacokinetics and metabolism.

The physicochemical properties of the two enantiomers of flecainide have been also described. In particular, Turgeon et al. described a stereoselective analytical method for the determination of the antiarrhythmic agent flecainide in human plasma. The resolution of the enantiomers is achieved by high-performance liquid chromatography (HPLC) on a normal phase silica column following derivatization with the optically active reagent (−)-methyl chloroformate [Turgeon et al., 1990].

Moreover, Alessi-Severini et al. described a stereospecific high-performance liquid chromatographic method for the determination of (R,S)-flecainide acetate in human plasma and urine. Flecainide diastereomers were separated after i) a single-step extraction of alkalinized samples performed with distilled diethyl ether, ii) the organic layer was evaporated and the drug was derivatized with 1-[(4-nitrophenyl)sulfonyl]-L-propyl chloride at 80 degrees C. for 2 h and iii) by high-performance liquid chromatography (HPLC) on a C18 reversed-phase column with a mobile phase consisting of acetonitrile:water:triethylamine (45:55:0.2) at a flow rate of 1 mL/min [Alessi-Severini et al., 1990].

Racemic flecainide acetate is a widely used class 1c antiarrhythmic agent, which is indicated for treating various types of arrhythmias. More specifically, it is used to regulate the rate and rhythm of the heart. The heart's pumping action is controlled by electrical signals that pass through the heart muscle. These electrical signals cause the two pairs of heart chambers (left and right arteria and ventricles) to contract in a regular manner to produce regular heartbeats. If the electrical activity in the heart is disturbed for any reason, irregular heartbeats (arrhythmias) of various types can result. Flecainide helps to treat arrhythmias by decreasing the sensitivity of the heart muscle cells to electrical impulses. This regulates the electrical conduction in the heart muscle and reduces disturbances in the heart rhythm. As a class I antiarrhythmic agent, flecainide interferes with the sodium channel.

Importantly, several studies have demonstrated that these cardiovascular effects are not mediated by a single enantiomer, both of them contributing to cardiovascular functions: Antiarrhythmic effects of flecainide and its enantiomers were assessed in two different animal models, chloroform-induced ventricular fibrillation in mice and ouabain-induced ventricular tachycardia in dogs. The two enantiomers were highly effective in suppressing both of these experimental arrhythmias and appeared to be essentially equipotent. No significant differences were found either between the two enantiomers or between the enantiomers and racemic flecainide [Banitt et al, 1986].

The effects of the enantiomers on action potential characteristics in canine cardiac Purkinje fibers were assessed, and they were shown to exert similar electrophysiological effects [Kroemer et al, 1989].

The effects of flecainide acetate racemate and its two enantiomers on voltage-operated sodium and potassium channels and on the sodium pump activity of non-myelinated fibers of the guinea-pig vagus nerve were studied with the sucrose-gap method. There was no significant difference in the effect caused by the enantiomers separately [Lie et al, 1989].

The effects of the enantiomers were evaluated in isolated canine Purkinje fibers using standard microelectrode techniques. The results suggest there is no significant difference between the effects of flecainide enantiomers on basic electro-physiological parameters of canine Purkinje fibers [Smallwood et al, 1989].

To conclude, all those studies have provided no evidence to indicate that administration of a single enantiomer, rather than the racemic drug, would offer any advantage.

According to a first aspect, the present invention therefore pertains to the use of flecainide, in vitro and in vivo, as an anti-connexin agent. In particular, the present invention relates to flecainide for use as an anti-connexin agent, or, in other words, for blocking gap junctions.

There are 21 genes coding for different connexin isoforms in humans, and different combinations of connexin monomers involved in the composition of the gap junctions are described. In particular, the connexins 26 (Cx 26), 30 (Cx 30), 30.2 (Cx30.2), 32 (Cx 32), 36 (Cx 36), 37 (Cx 37), 40 (Cx 40), 43 (Cx 43), 45 (Cx 45), 46 (Cx 46), and 47 (Cx 47) are expressed in human on cells of the Central or Peripheral Nervous System (Nakase & Naus, 2004).

The present inventors observed that flecainide is effective for inhibiting gap junctions made of all connexin they tested. In particular, and as disclosed in the experimental part below, flecainide is effective for inhibiting gap junctions made of connexin Cx40, Cx26, Cx30, Cx32, and/or Cx43. Importantly, this anti-connexin effect is similar to the one observed for well-known anti-connexin agents such as mefloquine and meclofenamic acid (MFA) (Juszczak & Swiergiel, 2009; Cruikshank et al, 2004; Harks et al, 2001). Higher inhibition levels were even reached for glial connexins Cx26, Cx30 and Cx43 (see FIGS. 1A-B).

The present invention therefore relates to the in vitro use of flecainide as an anti-connexin agent. Preferably, this agent can be used to inhibit gap junctions made of the connexins selected in the group consisting of: Cx23 (SEQ ID NO:1), Cx25 (SEQ ID NO:2), Cx26 (SEQ ID NO:3), Cx 30 (SEQ ID NO:4), Cx30.2 (SEQ ID NO:5), Cx30.3 (SEQ ID NO:6), Cx31 (SEQ ID NO:7), Cx31.1 (SEQ ID NO:8), Cx31.9 (SEQ ID NO:9), Cx32 (SEQ ID NO:10), Cx36 (SEQ ID NO:11), Cx37 (SEQ ID NO:12), Cx40 (SEQ ID NO:13), Cx40.1 (SEQ ID NO:14), Cx43 (SEQ ID NO:15), Cx45 (SEQ ID NO:16), Cx46 (SEQ ID NO:17), Cx47 (SEQ ID NO:18), Cx50 (SEQ ID NO:19), Cx59 (SEQ ID NO:20), and Cx62 (SEQ ID NO:21).

In a preferred embodiment of the invention, flecainide is used for blocking one or more of the connexins expressed in human cells of the Central or Peripheral Nervous System, that are selected in the group consisting of: Cx 26 (SEQ ID NO:3), Cx 30 (SEQ ID NO:4), Cx 30.2 (SEQ ID NO:5), Cx 32 (SEQ ID NO:10), Cx 36 (SEQ ID NO:11), Cx 37 (SEQ ID NO:12), Cx 40 (SEQ ID NO:13), Cx 43 (SEQ ID NO:15), Cx 45 (SEQ ID NO:16), Cx 46 (SEQ ID NO:17) and Cx 47 (SEQ ID NO:18).

In a more preferred embodiment, flecainide is used for blocking one or more of the connexins selected in the group consisting of: Cx40 (SEQ ID NO:13), Cx26 (SEQ ID NO:3), Cx30 (SEQ ID NO:4), Cx32 (SEQ ID NO:10), and Cx43 (SEQ ID NO:15).

In an even more preferred embodiment, flecainide is used for blocking one or more of the connexins selected in the group consisting of: Cx26 (SEQ ID NO:3), Cx30 (SEQ ID NO:4) and Cx43 (SEQ ID NO:15).

Due to its anti-connexin activity, flecainide can be used for the treatment of a number of disorders and conditions known to benefit from treatment by anti-connexin molecules.

These disorders and conditions include, but are not limited to: cancers, cardiovascular diseases, wounds, pain, migraines, epilepsy, neurological conditions and neurodegenerative diseases, infectious diseases, drug-induced liver injury, cytotoxicity induced by chemotherapeutic agents, ischemia and inflammatory disorders.

More preferably, flecainide can be used for the prevention and/or the treatment of cancers, wounds, migraines, epilepsy, infectious diseases, drug-induced liver injury, cytotoxicity induced by chemotherapeutic agents, ischemia and inflammatory disorders.

Even more preferably, flecainide can be used for the prevention and/or the treatment of wounds, migraines, infectious diseases, drug-induced liver injury, cytotoxicity induced by chemotherapeutic agents, and ischemia.

Even more preferably, flecainide can be used for the prevention and/or the treatment of drug-induced liver injury, cytotoxicity induced by chemotherapeutic agents, and ischemia.

According to a particular aspect of the present invention, flecainide is used as an agent for potentiating the effects of a psychotropic drug. These potentiating effects are illustrated below by experiments performed with modafinil (see FIGS. 2A-B to 4). As an anti-connexin agent, flecainide can potentiate the effects of any psychotropic drug (as shown in WO 2010/029131 and US 2011/172188, incorporated by reference).

The term "potentiate" in this case means that flecainide significantly increases the therapeutic effects of the psychotropic drug administered to the same patient. Thus, the combination of the psychotropic drug with flecainide makes it possible to reduce the doses of said psychotropic drug and therefore to limit the adverse effects of said psychotropic drug, and/or to obtain a stronger therapeutic effect without increasing the dose of said psychotropic drug.

In the present text, a "psychotropic drug" or "psychotropic agent" refers to any substance that acts primarily on the state of the central nervous system by modifying certain cerebral biochemical and physiological processes. Examples of psychotropic drugs which can be used in the context of the present invention include anesthetics, analgesics such as opioids, antipyretics and antimigraine preparations, antiepileptics, anti-Parkinson drugs such as anti-cholinergic and dopaminergic anti-Parkinson agents, psycholeptics such as antipsychotics, anxiolytics, hypnotics and sedatives, psychoanaleptics such as antidepressants, psychostimulants and anti-dementia drugs, as well as parasymptomimetics, antiaddiction drugs, antivertigo preparations etc. Non-limitative examples of specific molecules which can be advantageously used as psychotropic drugs according to the invention are listed in Table 1 below.

TABLE 1

| Psychotropic molecules | | | |
| --- | --- | --- | --- |
| Therapeutic category | Pharmacological sub-class | Chemical sub-class | Active agent |
| Anesthetics | 1. General anesthetics | 2. Ethers | 3. diethyl ether; vinyl ether |
| | | 4. Halogenated hydrocarbons | 5. halothane; chloroform; enflurane; trichloroethylene; isoflurane; desflurane; sevoflurane |
| | | 6. Barbiturates, plain | 7. methohexital; hexobarbital; |
| | | 8. Barbiturates in combination with other drugs | 9. narcobarbital |
| | | 10. Opioid anesthetics | 11. fentanyl; alfentanil; sufentanil; phenoperidine; anileridine; remifentanil; |
| | | 12. Other general anesthetics | 13. droperidol; ketamine; propanidid; alfaxalone; etomidate; propofol; sodium oxybate; nitrous oxide; esketamine; xenon; |

TABLE 1-continued

Psychotropic molecules

| Therapeutic category | Pharmacological sub-class | Chemical sub-class | Active agent |
|---|---|---|---|
| | 14. Local anesthetics | 15. Esters of aminobenzoic acid | 16. metabutethamine; procaine; tetracaine; chloroprocaine; benzocaine; |
| | | 17. Amides | 18. bupivacaine; lidocaine; mepivacaine; prilocaine; butanilicaine; cinchocaine; etidocaine; articaine; ropivacaine; levobupivacaine; bupivacaine; |
| | | 19. Esters of benzoic acid | 20. cocaine |
| | | 21. Other local anesthetics | 22. ethyl chloride; dyclonine; phenol; capsaicin |
| Analgesics | 23. Opioids | 24. Natural opium alkaloids | 25. opium; hydromorphone; nicomorphine; oxycodone; dihydrocodeine; diamorphine; papaveretum; morphine; codeine, |
| | | 26. Phenylpiperidine derivatives | 27. ketobemidone; pethidine; |
| | | 28. Diphenylpropylamine derivatives | 29. dextromoramide; piritramide; dextropropoxyphene; bezitramide; methadone, |
| | | 30. Benzomorphan derivatives | 31. pentazocine; phenazocine |
| | | 32. Morphinan derivatives | 33. butorphanol; nalbuphine |
| | | 34. Other opioids | 35. tilidine; tramadol; dezocine; meptazinol; tapentadol; |
| | 36. Other analgesics and antipyretics | 37. Salicylic acid and derivatives | 38. acetylsalicylic acid; aloxiprin; choline salicylate; sodium salicylate; salicylamide; salsalate; ethenzamide; morpholine salicylate; dipyrocetyl; benorilate; diflunisal; potassium salicylate; guacetisal; carbasalate calcium; imidazoles alicylate |
| | | 39. Pyrazolones | 40. phenazone; metamizole sodium; aminophenazone; propyphenazone; nifenazone; |
| | | 41. Anilides | 42. paracetamol; phenacetin; bucetin; propacetamol; |
| | | 43. Other analgesics and antipyretics | 44. rimazolium; glafenine; floctafenine; viminol; nefopam; ziconotide; methoxyflurane; nabiximols |
| | 45. Antimigraine Preparations | 46. Ergot alkaloids | 47. Dihydroergotamine; ergotamine; methysergide; lisuride; |
| | | 48. Corticosteroid derivatives | 49. flumedroxone |
| | | 50. Selective serotonin (5HT1) agonists | 51. sumatriptan; naratriptan; zolmitriptan; rizatriptan; almotriptan; eletriptan; frovatriptan |
| | | 52. Other antimigraine preparations | 53. pizotifen; clonidine; iprazochrome; dimetotiazine; oxetorone |
| Anti-epileptics | 54. Antiepileptics | 55. Barbiturates and derivatives | 56. methylphenobarbital; Phenobarbital; primidone; barbexaclone; metharbital |
| | | 57. Hydantoin derivatives | 58. ethotoin; phenytoin; amino(diphenylhydantoin) valeric acid; mephenytoin; fosphenytoin; |
| | | 59. Oxazolidine derivatives | 60. paramethadione; trimethadione; ethadione |
| | | 61. Succinimide derivatives | 62. Ethosuximide; phensuximide; mesuximide; |
| | | 63. Benzodiazepine derivatives | 64. clonazepam |
| | | 65. Carboxamide derivatives | 66. carbamazepine; oxcarbazepine; rufinamide; eslicarbazepine |

TABLE 1-continued

Psychotropic molecules

| Therapeutic category | Pharmacological sub-class | Chemical sub-class | Active agent |
|---|---|---|---|
| | | 67. Fatty acid derivatives | 68. valproic acid; valpromide; aminobutyric acid; vigabatrin; progabide; tiagabine |
| | | 69. Other antiepileptics | 70. sultiame; phenacemide; lamotrigine; felbamate; topiramate; gabapentin; pheneturide; levetiracetam; zonisamide; pregabalin; stiripentol; lacosamide; carisbamate; retigabine; beclamide |
| Anti-Parkinson drugs | 71. Anti-cholinergic agents | 72. Tertiary amines | 73. Trihexyphenidyl; biperiden; metixene; procyclidine; profenamine; dexetimide; phenglutarimide; mazaticol; bornaprine; tropatepine |
| | | 74. Ethers chemically close to antihistamines | 75. etanautine; orphenadrine |
| | | 76. Ethers of tropine or tropine derivatives | 77. benzatropine; etybenzatropine |
| | 78. Dopaminergic agents | 79. Dopa and dopa derivatives | 80. levodopa; decarboxylase inhibitor; COMT inhibitor; melevodopa; etilevodopa |
| | | 81. Adamantane derivatives | 82. amantadine |
| | | 83. Dopamine agonists | 84. bromocriptine; pergolide; dihydroergocryptine; esylate; ropinirole; pramipexole; cabergoline; apomorphine; piribedil; rotigotine |
| | | 85. Monoamine oxidase B inhibitors | 86. selegiline; rasagiline |
| | | 87. Other dopaminergic agents | 88. olcapone; entacapone; budipine |
| Psycho-leptics | 89. Antipschotics | 90. Phenothiazines with aliphatic side-chain | 91. chlorpromazine; levomepromazine; promazine; acepromazine; triflupromazine; cyamemazine; chlorproethazine |
| | | 92. Phenothiazines with piperazine structure | 93. dixyrazine; fluphenazine; perphenazine; prochlorperazine; thiopropazate; trifluoperazine; acetophenazine; thioproperazine; butaperazine; perazine |
| | | 94. Phenothiazines with piperidine structure | 95. periciazine; thioridazine; mesoridazine; pipotiazine |
| | | 96. Butyrophenone derivatives | 97. Haloperidol; trifluperidol; melperone; moperone; pipamperone; bromperidol; benperidol; droperidol; fluanisone |
| | | 98. Indole derivatives | 99. oxypertine; molindone; sertindole; ziprasidone |
| | | 100. Thioxanthene derivatives | 101. flupentixol; clopentixol; chlorprothixene; tiotixene; zuclopenthixol |
| | | 102. Diphenyl-butylpiperidine derivatives | 103. fluspirilene; pimozide; penfluridol |
| | | 104. Diazepines, oxazepines, thiazepines and oxepines | 105. loxapine; clozapine; olanzapine; quetiapine; asenapine; clotiapine |
| | | 106. Benzamides | 107. sulpiride; sultopride; tiapride; remoxipride; amisulpride; veralipride; levosulpiride |
| | | 108. Lithium | 109. lithium |
| | | 110. Other antipsychotics | 111. prothipendyl; risperidone; mosapramine; zotepine; aripiprazole; paliperidone |
| | 112. Anxiolytics | 113. Benzodiazepine derivatives | 114. chlordiazepoxide; medazepam; oxazepam; |

TABLE 1-continued

Psychotropic molecules

| Therapeutic category | Pharmacological sub-class | Chemical sub-class | Active agent |
|---|---|---|---|
| | | | potassiumclorazepate; lorazepam; adinazolam; bromazepam; clobazam; ketazolam; prazepam; alprazolam; halazepam; pinazepam camazepam; nordazepam; fludiazepam; ethyl loflazepate; etizolam; clotiazepam; cloxazolam; tofisopam; |
| | | 115. Diphenyl-methane derivatives | 116. hydroxyzine; captodiame; |
| | | 117. Carbamates | 118. meprobamate; emylcamate; mebutamate; |
| | | 119. Dibenzo-bicyclo-octadiene derivatives | 120. benzoctamine |
| | | 121. Azaspiro-decanedione derivatives | 122. buspirone |
| | | 123. Other anxiolytics | 124. Mephenoxalone; gedocarnil; etifoxine |
| | 125. Hypnotics and sedatives | 126. Barbiturates, plain | 127. Pentobarbital; amobarbital; butobarbital; barbital; aprobarbital; secobarbital; talbutal; vinylbital; vinbarbital; cyclobarbital; heptabarbital; reposal; methohexital; thiopental; etallobarbital; allobarbital; proxibarbal |
| | | 128. Aldehydes and derivatives | 129. chloral hydrate; chloralodol; acetylglycinamide; dichloralphenazone; paraldehyde |
| | | 130. Benzodiaze-pine derivatives | 131. flurazepam; nitrazepam; flunitrazepam; estazolam; triazolam; lormetazepam; temazepam; midazolam; brotizolam; quazepam; loprazolam; doxefazepam; cinolazepam |
| | | 132. Piperidinedione derivatives | 133. glutethimide; methyprylon; pyrithyldione |
| | | 134. Benzodiaze-pine related drugs | 135. zopiclone; zolpidem; zaleplon; eszopiclone |
| | | 136. Melatonin receptor agonists | 137. melatonin; ramelteon |
| | | 138. Other hypnotics and sedatives | 139. methaqualone; clomethiazole; bromisoval; carbromal; scopolamine; propiomazine; triclofosethchlorvynol; valerian; hexapropymate; bromides; apronal; valnoctamide; methylpentynol; niaprazine; dexmedetomidine |
| | | 140. Hypnotics and sedatives in combination, excl. barbiturates | 141. emepronium; dipiperonylaminoethanol |
| Psycho-analeptics | 142. Anti-depressants | 143. Non-selective monoamine reuptake inhibitors | 144. desipramine; imipramine; imipramine oxide; clomipramine; opipramol; trimipramine; lofepramine; dibenzepin; amitriptyline; nortriptyline; protriptyline; doxepin; iprindole; melitracen; butriptyline; do sulepin; amoxapine; dimetacrine; amineptine; maprotiline; quinupramine |
| | | 145. Selective serotonin reuptake inhibitors | 146. zimeldine; fluoxetine; citalopram; paroxetine; sertraline; alaproclate; fluvoxamine; etoperidone; escitalopram |
| | | 147. Monoamine oxidase inhibitors, non-selective | 148. isocarboxazid; nialamide; phenelzine; tranylcypromine; iproniazide; iproclozide |

TABLE 1-continued

Psychotropic molecules

| Therapeutic category | Pharmacological sub-class | Chemical sub-class | Active agent |
|---|---|---|---|
| | | 149. Monoamine oxidase A inhibitors | 150. moclobemide; toloxatone |
| | | 151. Other antidepressants | 152. oxitriptan; tryptophan; mianserin; nomifensine; trazodone; nefazodone; minaprine; bifemelane; viloxazine; oxaflozane; mirtazapine; bupropion; medifoxamine; tianeptine; pivagabine; venlafaxine; milnacipran; reboxetine; gepirone; duloxetine; agomelatine; desvenlafaxine |
| | 153. Psycho-stimulants, agents used for ADHD and nootropics | 154. Centrally acting sympathomimetics | 155. amphetamine; dexamfetamine; metamfetamine; methylphenidate; pemoline; fencamfamin; modafinil; armodafinil; fenozolone; atomoxetine; fenetylline; exmethylphenidate; lisdexamfetamine |
| | | 156. Xanthine derivatives | 157. caffeine; propentofylline |
| | | 158. Other psychostimulants and nootropics | 159. meclofenoxate; pyritinol; piracetam; deanol; fipexide; citicoline; oxiracetam; pirisudanol; linopirdine; nizofenone; aniracetam; acetylcarnitine; idebenone; prolintane; pipradrol; pramiracetam; adrafinil; vinpocetine; pitolisant; |
| | 160. Anti-dementia drugs | 161. Anti-cholinesterases | 162. tacrine; donepezil; rivastigmine; galantamine |
| | | 163. Other anti-dementia drugs | 164. memantine; ginkgo biloba |
| Other nervous system drugs | 165. Para-sympathomimetics | 166. Anti-cholinesterases | 167. neostigmine; pyridostigmine; distigmine; ambenonium; |
| | | 168. Choline esters | 169. carbachol; bethanechol |
| | | 170. Other parasympatho-mimetics | 171. pilocarpine; choline alfoscerate; cevimeline |
| | 172. Drugs used in addictive disorders | 173. Drugs used in nicotine dependence | 174. nicotine; varenicline |
| | | 175. Drugs used in alcohol dependence | 176. disulfiram; calcium carbimide; acamprosate; naltrexone; baclofene |
| | | 177. Drugs used in opioid dependence | 178. buprenorphine; levacetylmethadol; lofexidine; |
| | 179. Antivertigo preparations | 180. Antivertigo preparations | 181. betahistine; cinnarizine; flunarizine; acetylleucine |
| | 182. Other nervous system drugs | 183. Other nervous system drugs | 184. tirilazad; riluzole; xaliproden; amifampridine; tetrabenazine; fampridine; mazindol |

Preferably, the said psychotropic drug is selected in the group consisting of: dopaminergic, GABAergic, adrenergic, acetylcholinergic, serotoninergic, opioidergic, adenosinergic, ionotropic, histaminergic, IMAO, Catechol-O-methyl transferase, DOPA decarboxylase, noradrenergic and glutamatergic psychotropic effectors, as well as molecules having an effect on the hypocretin/orexin system (including hypocretin-1 and hypocretin-2).

The term "effector" herein refers to any substance activating or inhibiting, directly or indirectly, one or more neuroreceptors, as well as any substance that modifies the concentration of said neurotransmitter; therefore, an effector according to the present invention can be an agonist or an antagonist of said receptors.

It is shown in the examples below that said psychotropic drug is advantageously modafinil.

As a matter of fact, the present inventors have shown that flecainide potentiates the promnesiant and/or awakening effects of modafinil (see FIGS. 2A-B and 3), and that the modafinil/flecainide combination shows promising effects by reducing cataplectic-like events in mice. The precise mechanism of modafinil action has not been completely elucidated yet. In fact, it is known that modafinil acts on several molecular receptors, in particular on the dopamine, norepinephrine, serotonine, glutamate, GABA, orexine and histamine receptors (Ishizuka et al, 2012; Minzenberg et al, 2008). Therefore, modafinil acts as a GABAergic, dopaminergic, norepinephrinergic, serotoninergic, histaminergic, and glutamatergic effectors, and it has an effect on the hypocretin/orexin system (including hypocretin-1 and hypocretin-2).

Any compound modulating the same molecular receptors as modafinil can be advantageously associated with flecainide.

Thus, in a preferred embodiment, the psychotropic drug which is associated with flecainide acts on the very same receptors as modafinil does. The psychotropic drug associated with flecainide is therefore preferably selected in the group consisting of: GABAergic, dopaminergic, norepinephrinergic, serotoninergic, histaminergic, and glutamatergic effectors. Also, it may have an effect on the hypocretin/orexin system (including hypocretin-1 and hypocretin-2).

According to a specific embodiment, the said psychotropic drug is a dopaminergic effector selected in the group consisting of: ADX-N05 (formely "YKP10A", having the formula: (R)-(beta-amino-benzenepropyl) carbamate monohydrochloride), amphetamine, loxapine, acepromazine, methylphenidate, pergolide, lisuride, bromocriptine, dopamine, ropinirole, apomorphine, aripiprazole, sulpiride, amisulpride, sultopride, tiapride, pimozide, risperidone, haloperidol, penfluridol, zuclopenthixol or bupropion.

According to another specific embodiment, the said psychotropic drug is a GABAergic effector selected in the group consisting of: tiagabine, topiramate, clorazepate, diazepam, clonazepam, oxazepam, lorazepam, bromazepam, lormetazepam, nitrazepam, clotiazepam, aiprozolam, estazolam, triazolam, loprazolam, etifoxin, meprobamate, zopiclone, zolpidem, pregabaline, gabapentine, phenobarbital, felbamate and vigabatrin.

According to another specific embodiment, the said psychotropic drug is a serotoninergic effector selected in the group consisting of: chlorpromazine, trimipramine, clozapine, olanzapine, cyamemazine, flupentixol, nefopam, fluvoxamine, clomipramine, sertraline, fluoxetine, citalopram, escitalopram, paroxetine, amitriptyline, duloxetine, venlafaxine, buspirone, carpipramine, zolmitriptan, sumatriptan, naratriptan, indoramine, ergotamine, ergotamine tartrate, pizotifene, pipamperone, methysergide, pizotyline, milnacipran, viloxazine, tianeptine, hypericum and lithium.

According to another specific embodiment, the said psychotropic drug is a histaminergic effector selected in the group consisting of: acrivastine, alimemazine, antazoline, astemizole, azatadine, azelastine, brompheniramine, buclizine, carbinoxamine, carebastine, cetirizine, chlorcyclizine, chlorpheniramine, cinnarizine, clemastine, clemizole, clocinizine, clonidine, cyclizine, cyproheptadine, descarboethoxyloratidine, dexchlorpheniramine, dimenhydrinate, dimethindene, dimethothiazine, diphenhydramine, diphenylpyraline, doxylamine, ebastine, efletirizine, epinastine, fexofenadine, hydroxyzine, ketotifen, levocabastine, loratidine, meclizine, mequitazine, methdilazine, mianserin, mizolastine, niaprazine, noberastine, norastemizole, oxatomide, oxomemazine, phenbenzamine, pheniramine, picumast, promethazine, pyrilamine, temelastine, terfenadine, trimeprazine, tripelennamine, triprolidine, ranitidine, cimetidine, famotidine, nizatidine, tiotidine, zolantidine, ciproxifan, pitolisant and ritanserine.

According to another specific embodiment, the said psychotropic drug is a hypocretin/orexin modulator selected in the group consisting of: EMPA, SB-334867, SB-674042, SB-408124, GSK1059865, almorexant, suvorexant, MK-6096, DORA-1, DORA-22, DORA-12, SB-649868, JNJ-1037049 (described in Gotter et al, 2012)).

According to another specific embodiment, the said psychotropic drug is a norepinephrinergic effector selected in the group consisting of: (R)-3-nitrobiphenyline, 2-fluoronorepinephrine, 4-NEMD, 5-fluoronorepinephrine, 6-fluoronorepinephrine, abediterol, albuterol, amibegron, amidephrine, amitraz, anisodamine, anisodine, apraclonidine, arbutamine, arformoterol, arotinolol, bambuterol, befunolol, bitolterol, brimonidine, bromoacetylalprenololmenthane, broxaterol, buphenine, cannabivarin, carbuterol, cimaterol, cirazoline, clenbuterol, denopamine, deterenol, detomidine, dexmedetomidine, dihydroergotamine, dipivefrine, dobutamine, dopexamine, ephedrine, epinephrine, esproquin, etafedrine, ethylnorepinephrine, etilefrine, fenoterol, formoterol, guanabenz, guanfacine, guanoxabenz, hexoprenaline, higenamine, indacaterol, indanidine, isoetarine, isoprenaline, isoproterenol, isoxsuprine, labetalol, levonordefrin, levosalbutamol, lofexidine, mabuterol, medetomidine, metaraminol, methoxamine, methoxyphenamine, methyldopa, midodrine, mivazerol, n-isopropyloctopamine, naphazoline, norepinephrine, octopamine, orciprenaline, oxyfedrine, oxymetazoline, phenylephrine, phenylpropanolamine, piperoxan, pirbuterol, prenalterol, procaterol, pseudoephedrine, ractopamine, reproterol, rilmenidine, rimiterol, ritodrine, romifidine, salbutamol, salmeterol, solabegron, synephrine, talipexole, terbutaline, tetrahydrozoline, tizanidine, tolonidine, tretoquinol, tulobuterol, urapidil, xamoterol, xylazine, xylometazoline, zilpaterol, and zinterol.

According to another specific embodiment, the said psychotropic drug is a glutamatergic effector selected in the group consisting of: memantine, amantadine, MK-801, ketamine, norketamine, dextromethorphan, levomethorphan, dextrorphan, levorphanol, phencyclidine, PCA, CNS-1102, ramacemide, pentamidine, and 9-aminoacridine (described in Traynelis et al, 2010).

Preferably, said psychotropic drug is not flupirtine.

The potentiating effects of flecainide can be achieved by administrating same to a patient, either before, at the same time, of after administration of the psychotropic drug to said patient.

Consequently, the present invention describes a method for treating a patient with psychiatric and/or neurodegenerative disorders, including the administration to said patient of a) flecainide and b) at least one psychotropic drug as mentioned above, in which said compounds a) and b) are administered simultaneously, separately or spread out over time.

Patients needing this treatment may have psychiatric, neurologic and/or neurodegenerative disorders included in the group consisting of: excessive daytime sleepiness (EDS), sleep disorders, insufficient sleep time, central sleep apnea, narcolepsy (with or without cataplexy), obstructive sleep apnea/hypopnea (SAHOS), idiopathic hypersomnia, Kleine-Levin syndrome, circadian rhythm disorders, shift work sleep disorder, jet-lag, disorders after sleep restriction or sleep deprivation (attention disorders, alertness disorders, sleepiness), restless legs syndrome (RLS) and Periodic Lim Movement Disorders (PLMD), insomnia, parasomnia, attention deficit hyperactivity disorder (ADHD), post-traumatic stress disorder (PTSD), disorders commonly associated with somnolence or sleepiness (such as Parkinson disease, multiple sclerosis, stroke, neuromuscular disorders or structural brain disorders, respiratory disorders, chronic renal failure, liver failure, rheumatologic disorders), medication-induced somnolence (due to benzodiazepines, barbiturates, sleeping pills, antidepressants, anti-psychotics . . . ), mood disorders, anxiety disorders, schizophrenia, tinnitus, depression, malaise, dementia, bipolar disorder, obesity, hyperphagia, manic episode, obsessive-compulsive disorder, senility, dependence or addiction (to games, drugs, alcohol, tobacco, etc.), fecal or urinary incontinence, premature ejaculation, breathing difficulty and fatigue, notably due to cancer, neurodegenerative disorders, menopause, traumatic brain injuries, viral infection or post-myelitis, or to fibromyalgia.

Excessive daytime sleepiness (EDS) occurs daily, recurring typically every 2 h, although this can vary widely. Sleepiness is exacerbated when the patient is physically inactive. The sleep episodes have several characteristics (Dauvilliers I. et al, 2007 and Boulos et al, 2010):

They are often irresistible, despite the individual making desperate efforts to fight the urge to sleep;

They are usually short, although their length can vary with environmental factors (eg, the duration can increase with passive activities such as watching television);

They are frequently associated with dreaming;

They typically restore normal wakefulness for up to several hours.

EDS characterizes several conditions or diseases: insufficient sleep time, central sleep apnea, narcolepsy (with or without cataplexy), obstructive sleep apnea/hypopnea (SAHOS), idiopathic hypersomnia, recurrent hypersomnia (Kleine-Levin syndrome), circadian rhythm disorders (jet lag), disorders after sleep restriction or sleep deprivation (attention disorders, alertness disorders, sleepiness), restless legs syndrome (RLS) and Periodic Lim Movement Disorders (PLMD), neurological conditions commonly associated with sleepiness (such as Parkinson disease, multiple sclerosis, stroke, neuromuscular disorders or structural brain disorders), medical conditions commonly associated with sleepiness (respiratory disorders, chronic renal failure, liver failure, rheumatologic disorders), mood disorders, anxiety disorders, schizophrenia, or medication-induced somnolence (due to benzodiazepines, barbiturates, sleeping pills, antidepressants, anti-psychotics . . . ).

Cataplexy is characterized by a sudden drop of muscle tone triggered by emotional factors, most often by positive emotions such as laughter, repartee, pleasant surprise (e.g., seeing friends in the street or scoring a goal), or by anger, but almost never by stress, fear, or physical effort. Many neurophysiological and pharmaceutical studies indicate that cataplexy shares common neurophysiological mechanisms with REM sleep atonia (Dauvilliers I. et al, 2007).

In the case of simultaneous use, the two components of the treatment are administered to the patient simultaneously. According to this embodiment of the present invention, the two components can be packaged together, in the form of a mixture, or separately, then mixed spontaneously before being administered together to the patient. Alternatively, the two components are administered simultaneously, but separately. In particular, the routes of administration of the two components may be different. The administration can also be performed at different sites. In another embodiment, the two components are administered sequentially or spaced apart over time, for example in the same day or at an interval ranging from several minutes to several days.

Since flecainide potentiates the effects of psychotropic drugs, it can advantageously be used for reducing the doses of said psychotropic drug, thereby limiting the adverse effects of said psychotropic drug, and/or reducing the risks of failure and withdrawal.

The effective equivalent dose of a psychotropic drug, i.e., the psychotropic drug dose that, when administered in combination with flecainide, induces a physiological effect or a pharmacological signature similar or identical to that of the psychotropic drug alone administered at the active pharmacological dose, can be determined by the methods disclosed in WO2010/029131 and US 2011/172188.

According to another aspect, the present invention pertains to a composition, especially a pharmaceutical composition, comprising flecainide and at least one psychotropic drug. This composition is preferably formulated for patients with psychiatric and/or neurodegenerative disorders, as disclosed above. In addition to flecainide and to said psychotropic drug, the composition can comprise any pharmaceutical vehicle, stabilizer, adjuvant and the like as frequently used in the art.

Examples of pharmaceutically acceptable vehicles include, but are not limited to: water; aqueous vehicles such as, but not limited to, sodium chloride solution, Ringer's solution, dextrose solution, dextrose and sodium chloride solution, and lactated Ringer's solution; water-miscible vehicles such as, but not limited to, ethyl alcohol, polyethylene glycol, and polypropylene glycol; and nonaqueous vehicles such as, but not limited to, corn oil, cottonseed oil, peanut oil, sesame oil, ethyl oleate, isopropyl myristate, and benzyl benzoate.

According to a preferred embodiment, this composition is formulated for oral administration (including buccal cavity or sublingually). Other interesting formulations include formulations for intraperitoneal (i.p.), intravenous (i.v.), subcutaneous (s.c.), intramuscular (i.m.), transcutaneous, transdermal, intrathecal and intracranial administrations. Still other formulations include epidural, submucosal, intranasal, ocular cul-de-sac and rectal routes of administration, as well as administration by pulmonary inhalation.

A variety of administration means, including but not limited to capsules, tablets, syrups, creams and ointments, suppositories, patches or any reservoir capable of containing and dispensing flecainide and the psychotropic drug, can be used for formulating the above-described compositions.

In the compositions according to the invention, the psychotropic drug is as described above.

In a preferred embodiment, said psychotropic drug is used for treating narcolepsy and is therefore selected in the group consisting of: caffeine, mazindol, sodium oxybate, pitolisant, amphetamine, methylphenidate, (R)-(beta-aminobenzenepropyl) carbamate mono-hydrochloride, modafinil and armodafinil.

In a preferred embodiment, the composition of the invention contains between 1 to 1000 mg, preferably 5 to 800 mg of the psychotropic drug, depending of its nature. A preferred posology would be to administer to the patient between 1 to 1000 mg/day, more preferably between 5 to 800 mg/day of the psychotropic drug.

According to another preferred embodiment, the composition of the invention contains between 1 to 200, preferably 1 to 100 mg of flecainide. A preferred posology would be to administer to the patient between 1 to 200, preferably 1 to 100 mg/day of flecainide.

More preferably, said flecainide is the R enantiomer disclosed on FIG. 5A.

In a more preferred embodiment, flecainide is associated with the psychotropic drug modafinil.

Figure 5C:
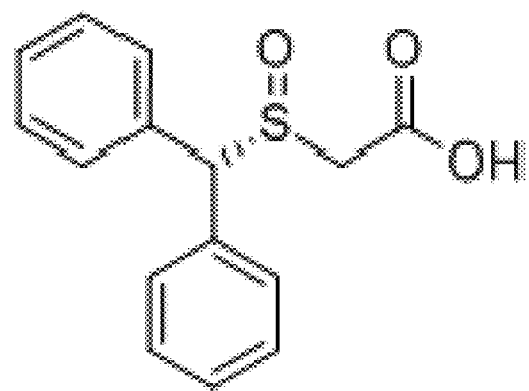
Figure 5D:
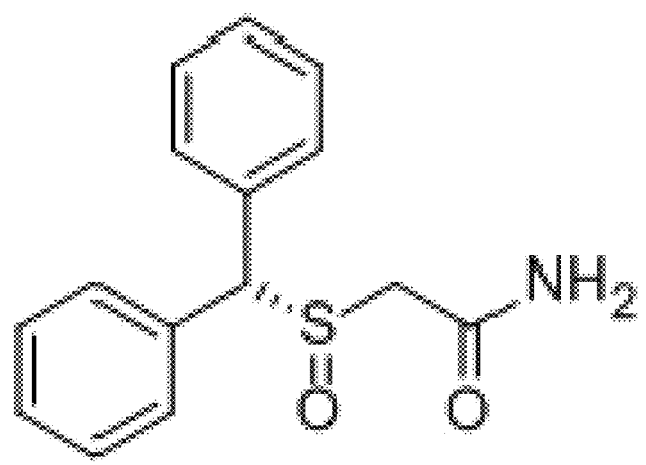

By "modafinil" is herein meant the 2-[(diphenylmethyl) sulfinyl] acetamide (Provigil, see FIG. 5C), as well as its precursors or prodrugs such as adrafinil (Dubey et al, 2009) which can be metabolized in the human body and its active derivatives. More precisely, the term "Modafinil" herein designates any form of modafinil (racemate, R-modafinil, S-modafinil, etc.), as well as its precursors which can be metabolized in the human body and its derivatives. FIGS. 5C-D show the formulas of R-Modafinil (FIG. 5C) and S-Modafinil (FIG. 5D).

Modafinil is an analeptic drug prescribed essentially for the treatment of narcolepsy, shift work sleep disorder, and excessive daytime sleepiness associated with obstructive sleep apnea. Besides these wake-promoting properties, modafinil also improves working memory and episodic memory, and other processes dependent on prefrontal cortex and cognitive control (Minzenberg M J et al, 2008).

The present inventors have shown that, surprisingly, flecainide strongly potentiates in vivo the waking effects of Modafinil, whereas it has no effect on wake duration on its own (example 2). Moreover, flecainide strongly potentiates in vivo the cognitive activity of Modafinil, whereas it has no promnesiant effect on its own (example 3). This synergistic activity could be explained by the fact that flecainide strongly extends the duration of Modafinil treatment (example 4). On the other hand, the present inventors herein describes that the flecainide/modafinil combination has a synergistic effect on cataplectic-like phenotype in narcoleptic mice (example 5) and is all the more surprising than either flecainide or modafinil has no effect on this phenotype (FIG. 6B). In a preferred embodiment, the present invention thus pertains to flecainide, for use for potentiating the promnesiant and/or awakening effects of modafinil, and/or for improving its safety, and/or for increasing the duration of action of modafinil in patients in need thereof, especially in patients suffering from: excessive daytime sleepiness (EDS), sleep disorders, insufficient sleep time, central sleep apnea, narcolepsy (with or without cataplexy), obstructive sleep apnea/hypopnea (SAHOS), idiopathic hypersomnia, Kleine-Levin syndrome, circadian rhythm disorders, shift work sleep disorder, jet-lag, disorders after sleep restriction or sleep deprivation (attention disorders, alertness disorders, sleepiness), restless legs syndrome (RLS) and Periodic Lim Movement Disorders (PLMD), insomnia, parasomnia, attention deficit hyperactivity disorder (ADHD), post-traumatic stress disorder (PTSD), disorders commonly associated with somnolence or sleepiness (such as Parkinson disease, multiple sclerosis, stroke, neuromuscular disorders or structural brain disorders, respiratory disorders, chronic renal failure, liver failure, rheumatologic disorders), medication-induced somnolence (due to benzodiazepines, barbiturates, sleeping pills, antidepressants, anti-psychotics . . . ), mood disorders, anxiety disorders, schizophrenia, tinnitus, depression, malaise, dementia, bipolar disorder, obesity, hyperphagia, manic episode, obsessive-compulsive disorder, senility, dependence or addiction (to games, drugs, alcohol, tobacco, etc.), fecal or urinary incontinence, premature ejaculation, breathing difficulty and fatigue, notably due to cancer, neurodegenerative disorders, menopause, traumatic brain injuries, viral infection or post-myelitis, or to fibromyalgia, which have been proposed to be treated by modafinil.

In a more preferred embodiment, the present invention specifically pertains to flecainide, for use for potentiating the awakening effects of modafinil, and/or for improving its safety, and/or for increasing the duration of action of modafinil in patients suffering from: excessive daytime sleepiness (EDS), sleep disorders, insufficient sleep time, central sleep apnea, narcolepsy (with or without cataplexy), obstructive sleep apnea/hypopnea (SAHOS), idiopathic hypersomnia, Kleine-Levin syndrome, circadian rhythm disorders, shift work sleep disorder, jet-lag, disorders after sleep restriction or sleep deprivation (attention disorders, alertness disorders, sleepiness), restless legs syndrome (RLS) and Periodic Lim Movement Disorders (PLMD), insomnia, parasomnia, attention deficit hyperactivity disorder (ADHD), post-traumatic stress disorder (PTSD), disorders commonly associated with somnolence or sleepiness (such as Parkinson disease, multiple sclerosis, stroke, neuromuscular disorders or structural brain disorders, respiratory disorders, chronic renal failure, liver failure, rheumatologic disorders), medication-induced somnolence (due to benzodiazepines, barbiturates, sleeping pills, antidepressants, anti-psychotics . . . ), mood disorders, anxiety disorders, schizophrenia, tinnitus, depression, malaise, dementia, bipolar disorder, obesity, hyperphagia, manic episode, obsessive-compulsive disorder, senility, dependence or addiction (to games, drugs, alcohol, tobacco, etc.), fecal or urinary incontinence, premature ejaculation, breathing difficulty and fatigue, notably due to cancer, neurodegenerative disorders, menopause, traumatic brain injuries, viral infection or post-myelitis, or to fibromyalgia, for which modafinil has been proposed or authorized.

In a preferred embodiment, the present invention specifically pertains to flecainide, for use for potentiating the awakening effects of modafinil, and/or for improving its safety, and/or for increasing the duration of action of modafinil in patients suffering from excessive daytime sleepiness (EDS).

In another preferred embodiment, the present invention relates to flecainide, for use for potentiating the awakening effects of modafinil, and/or for improving its safety, and/or for increasing the duration of action of modafinil in patients suffering from conditions or diseases involving EDS, that are for example: insufficient sleep time, central sleep apnea, narcolepsy (with or without cataplexy), obstructive sleep apnea/hypopnea (SAHOS), idiopathic hypersomnia, recurrent hypersomnia (Kleine-Levin syndrome), circadian rhythm disorders (jet lag), disorders after sleep restriction or sleep deprivation (attention disorders, alertness disorders and sleepiness), restless legs syndrome (RLS) and Periodic Lim Movement Disorders (PLMD), neurological conditions commonly associated with sleepiness (such as Parkinson disease, multiple sclerosis, stroke, neuromuscular disorders or structural brain disorders), medical conditions commonly associated with sleepiness (respiratory disorders, chronic renal failure, liver failure, rheumatologic disorders), mood disorders, anxiety disorders, schizophrenia, or medication-induced somnolence (due to benzodiazepines, barbiturates, sleeping pills, antidepressants, anti-psychotics . . . ).

In another preferred embodiment, the present invention relates to a modafinil/flecainide combination product, for use for treating cataplexy in narcoleptic patients.

It is to be noted that the potentiation of the effects of modafinil by flecainide enables a reduction of the dose of modafinil, and hence a reduction of its side-effects. As a consequence, some applications of modafinil, for which this drug was not approved because of its side-effects and possible risks associated thereto, can now be envisioned, such as its use as a performance-enhancing and/or brain-boosting agent. According to a particular embodiment, the present invention thus pertains to a performance-enhancing product comprising flecainide and modafinil.

In another preferred embodiment, the present invention specifically pertains to the use of flecainide and modafinil for enhancing the memory of healthy subjects and/or to maintain them awake for long-lasting periods of time and/or to treat cataplexy in narcoleptic patients. These subjects can be for example individuals that need to memorize a lot of information and/or to remain awake for long lasting periods. In a preferred embodiment, said subjects are humans (e.g., security agents, students, etc.).

In a particular embodiment, the present invention also relates to a composition comprising flecainide and modafinil, which can advantageously be used for treating diseases and conditions including but not limited to excessive daytime sleepiness (EDS), narcolepsy (with or without cataplexy), obstructive sleep apnea/hypopnea (SAHOS), shift work sleep disorder, disorders after sleep restriction or sleep deprivation (attention disorders, alertness disorders, sleepiness), restless leg syndrome, hypersomnia, idiopathic hypersomnia and fatigue, notably due to cancer, jet-lag, neurodegenerative disorders, menopause, traumatic brain injuries, viral infection or post-myelitis, or to fibromyalgia. In particular, this composition can be used for treating cataplexy in narcoleptic patients.

This composition can also be used for enhancing the memory of healthy subjects and/or for maintaining them awake for long-lasting periods of time. Typical periods of time are for example 6 hours, preferably 12 hours.

The present invention moreover relates specifically to the use of flecainide and modafinil in the preparation of a medicament that is intended to be used for treating diseases and conditions such as excessive daytime sleepiness (EDS), narcolepsy (with or without cataplexy), obstructive sleep apnea/hypopnea (SAHOS), shift work sleep disorder, restless leg syndrome, hypersomnia, idiopathic hypersomnia and fatigue, notably due to cancer, neurodegenerative disorders, menopause, traumatic brain injuries, viral infection or post-myelitis, or to fibromyalgia.

In a preferred embodiment, the present invention relates to the use of flecainide and modafinil in the preparation of a medicament that is intended to be used for treating cataplexy in narcoleptic patients.

In addition to modafinil and flecainide, the composition/medicament of the invention can comprise other agents such as vitamin C, vitamin B6, magnesium, L-arginine, L-glutamine, L-citrulline, taurine, caffeine, etc. According to a particular embodiment, this product can be sold over-the-counter. It can be formulated, for example, as an OTC medicine or as a food supplement.

In a preferred embodiment, the composition of the invention contains between 1 to 1000 mg, preferably between 5 to 800 mg, and more preferably between 5 to 600 mg of the modafinil. According to another preferred embodiment, the composition of the invention is formulated so that 5 to 800, preferably 5 to 600 mg/day of modafinil are administered to a patient in need thereof, in one, two or more takings.

According to another preferred embodiment, the composition of the invention contains between 1 to 200, preferably 1 to 100 mg of flecainide. According to another preferred embodiment, the composition of the invention is formulated so that 1 to 200, preferably 1 to 100 mg/day of flecainide are administered to a patient in need thereof, in one, two or more takings. In a more preferred embodiment, said flecainide is the R enantiomer disclosed on FIG. 5A.

In a final aspect, the present invention relates to a combination product comprising flecainide and modafinil, for simultaneous, separated or staggered use for preventing and/or treating excessive daytime sleepiness (EDS), narcolepsy (with or without cataplexy), obstructive sleep apnea/hypopnea (SAHOS), shift work sleep disorder, restless leg syndrome, hypersomnia, idiopathic hypersomnia and fatigue, notably due to cancer, jet-lag, neurodegenerative disorders, menopause, traumatic brain injuries, viral infection or post-myelitis, or to fibromyalgia. This combination product is preferably used for preventing and/or treating cataplexy in narcoleptic patients.

Other characteristics of the invention will also become apparent in the course of the description which follows of the biological assays which have been performed in the framework of the invention and which provide it with the required experimental support, without limiting its scope.

LEGENDS TO THE FIGURES

Figure 1B:
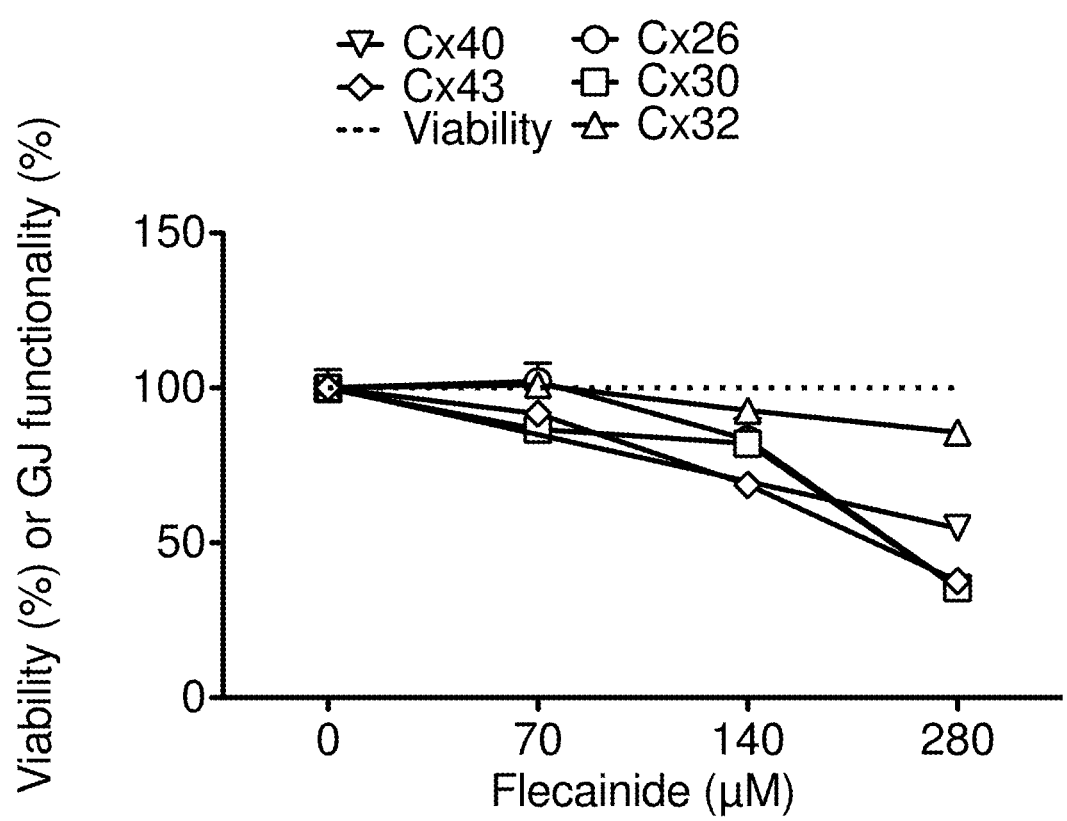

FIGS. 1A-B: Inhibition of the human connexins functionality by flecainide. Rin-Cx26 cells, Rin-Cx30 cells, Rin-Cx32 cells, Rin-CX40 cells and Rin-Cx43 cells are cultured in the presence of flecainide (280 µM), mefloquine (10 µM) and MFA (100 µM) for 4 hours. The transfer of fluorochrome by gap junctions (composed of connexins) is evaluated by flow cytometry (1A and 1B). Viability of the cells treated with flecainide is shown on FIG. 1B.

Figure 2A:
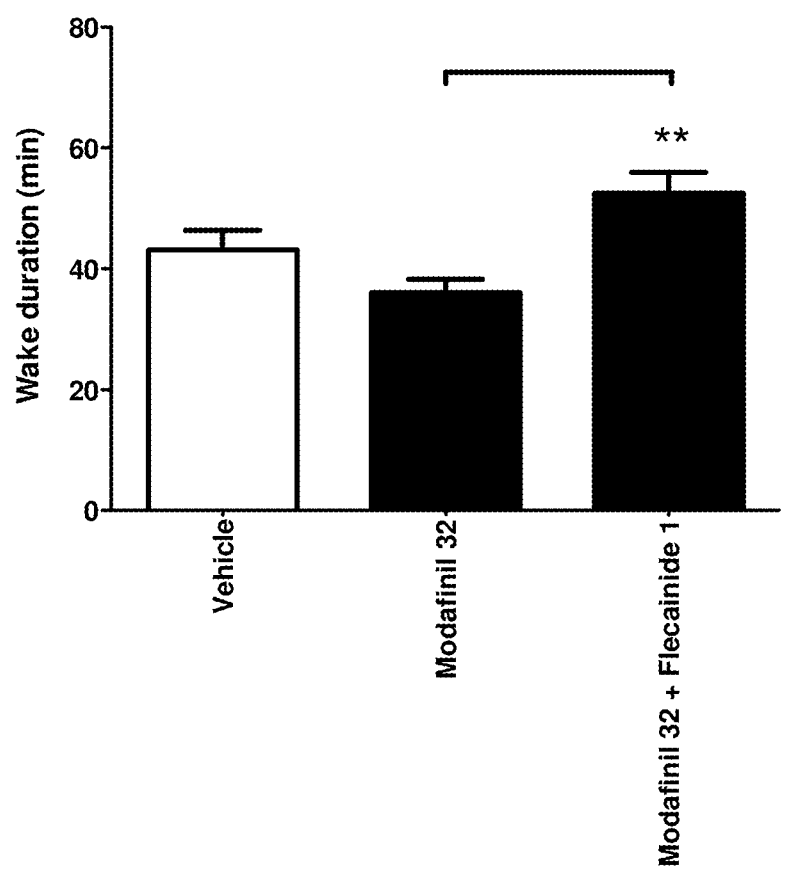
Figure 2B:
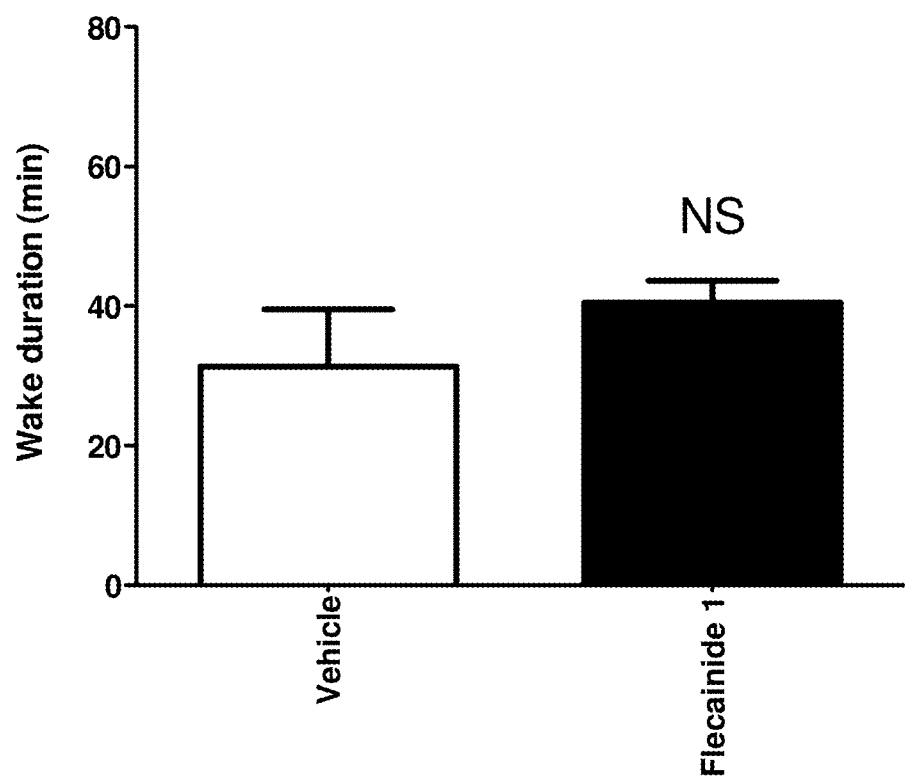

FIGS. 2A-B: Efficiency of flecainide for potentiating the awakening effect of modafinil. Mice (n=8 per batch) were orally treated by either modafinil (32 mg/kg) or modafinil (32 mg/kg) and flecainide (1 mg/kg) (FIG. 2A) or flecainide alone (1 mg/kg) (FIG. 2B) and replaced in their home cage. The wake duration was measured using polygraphic analyses.

Figure 3:
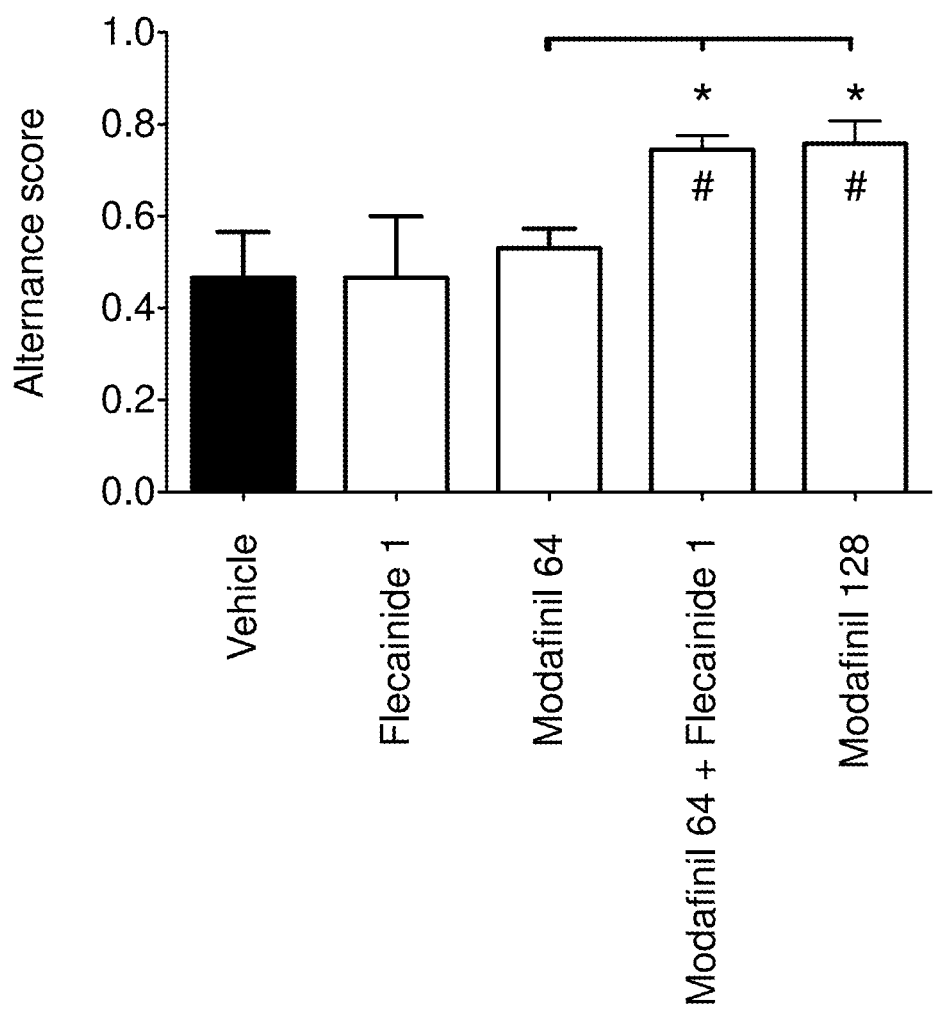

FIG. 3: Efficacy of flecainide for potentiating the promnesiant effect of modafinil. Mice (n=6 to 23 per batch) are tested in the T-maze. They were intraperitoneally treated by either modafinil (64 mg/kg or 128 mg/kg) or modafinil (64 mg/kg) and flecainide (1 mg/kg) or flecainide alone (1 mg/kg). The graphic represents the percentage of alternation after 6 trials, 50% corresponding to a random alternation.

Figure 4:
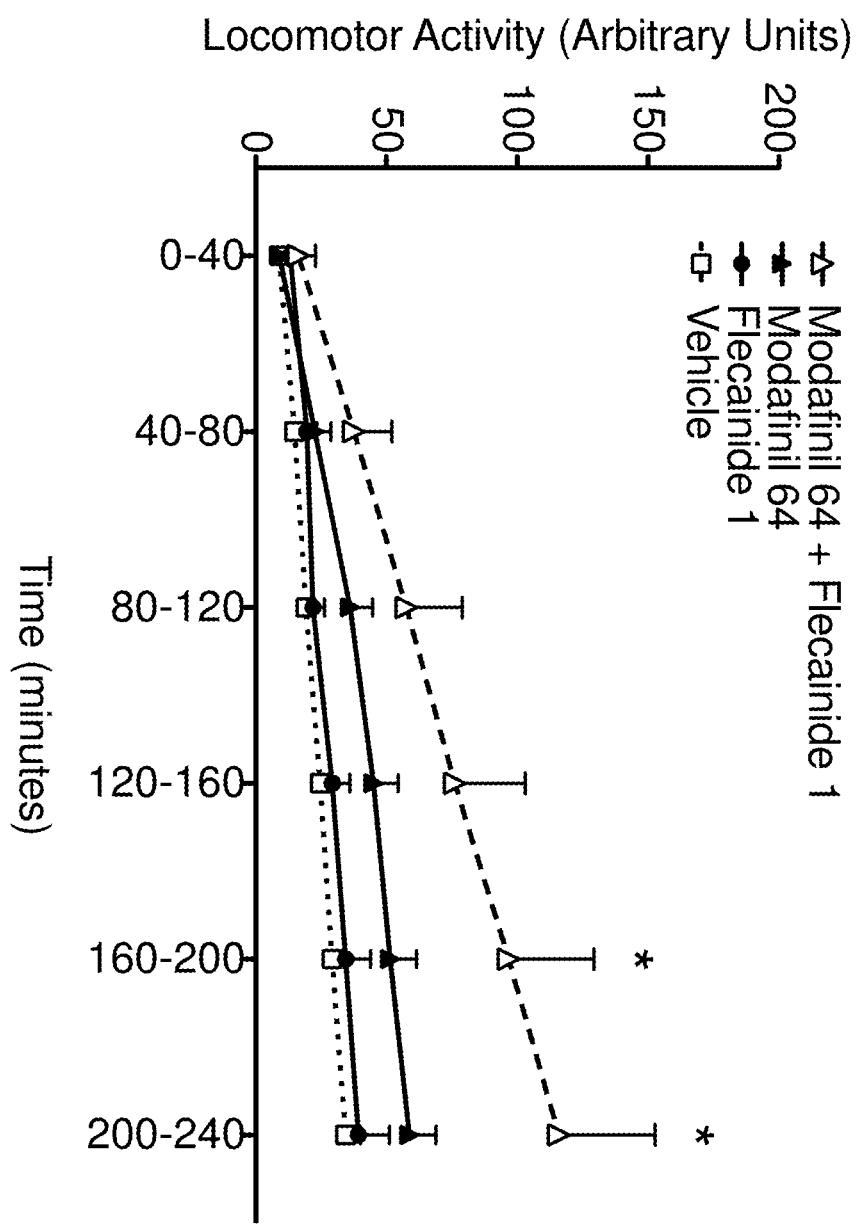

FIG. 4: Efficacy of flecainide for potentiating the locomotor effect of modafinil. Mice (n=8 per batch) were orally treated by either modafinil (64 mg/kg) or modafinil (64 mg/kg) and flecainide (1 mg/kg) or flecainide alone (1 mg/kg) and replaced in their home cage. The locomotor activity was measured using videotracking device.

FIGS. 5A-D: Molecular structure of FIG. 5A. R-flecainide; FIG. 5B. S-flecainide; FIG. 5C. R-Modafinil, FIG. 5D. S-Modafinil.

Figure 6A:
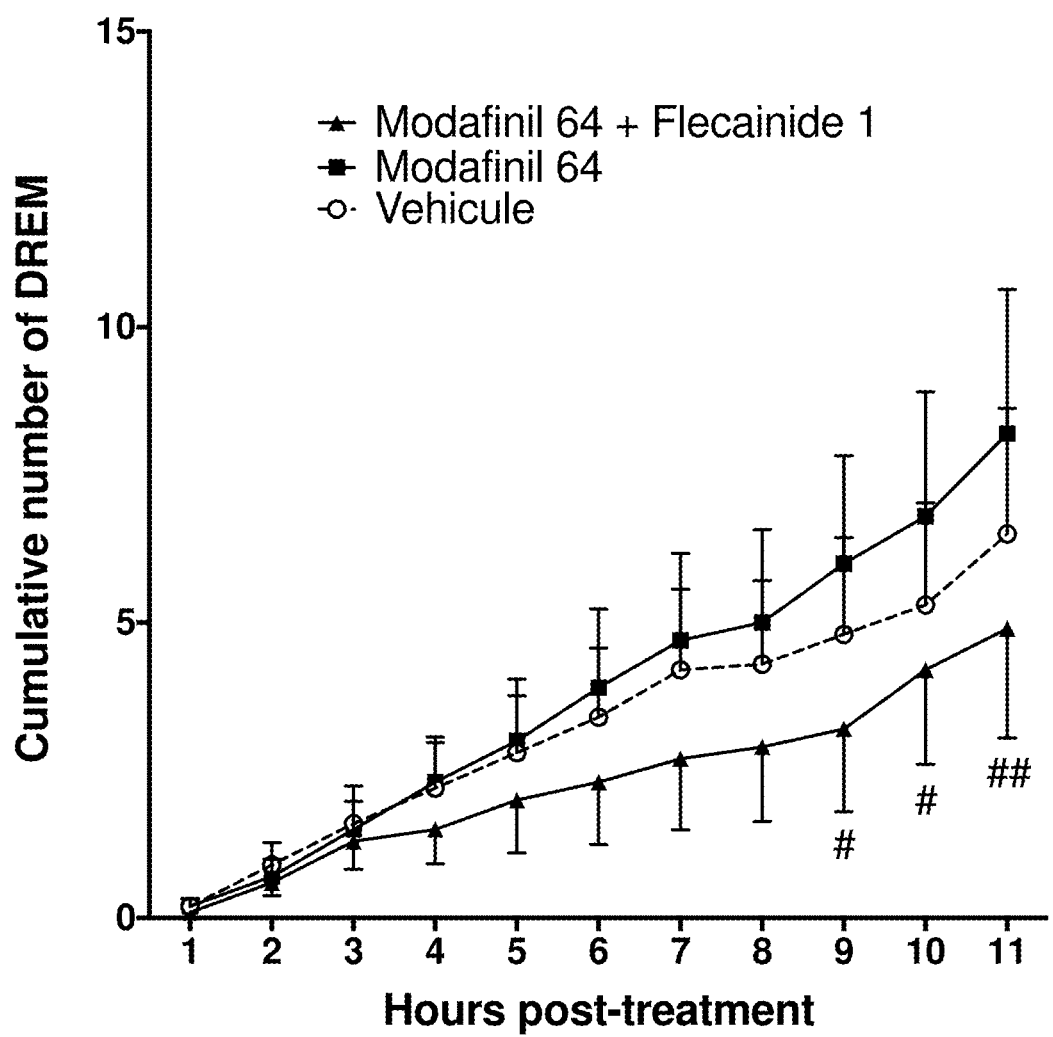
Figure 6B:
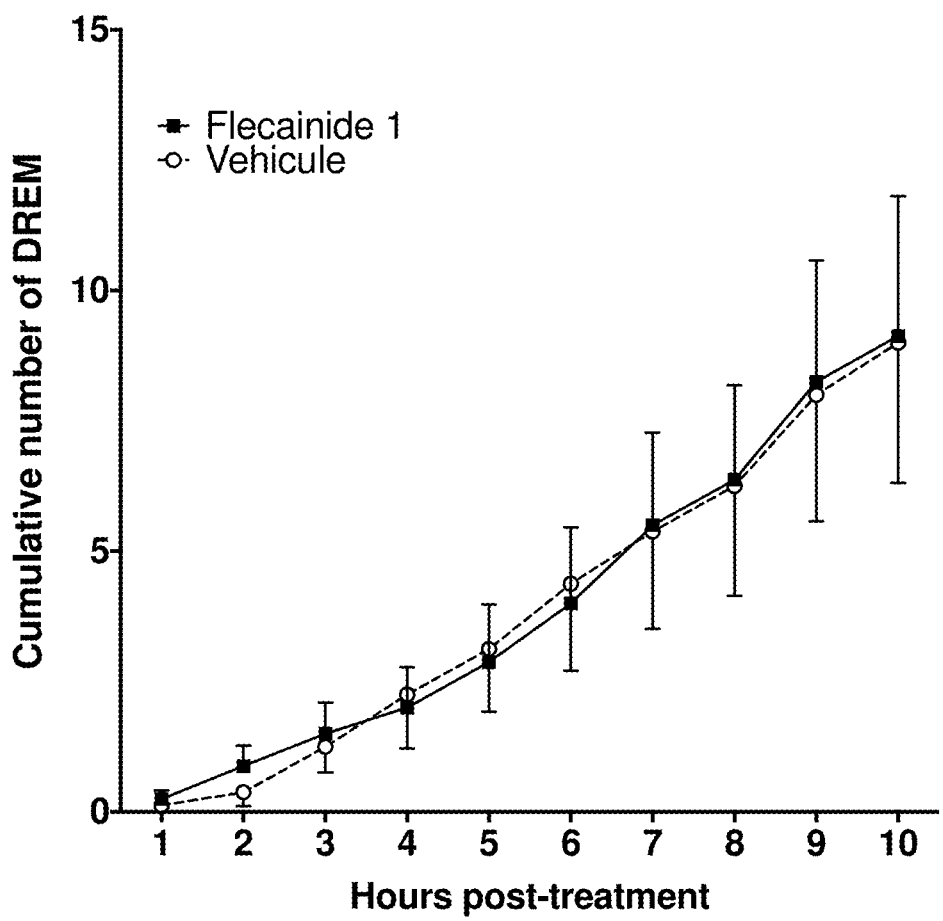

FIGS. 6A-B: Number of episodes of OREM/DREM phases in narcoleptic mice (Ox−/−) treated by modafinil/flecainide (FIG. 6A) or flecainide alone (FIG. 6B). (FIG. 6A). Oral treatment of Ox−/− male mice with modafinil 64 mg/kg with flecainide 1 mg/kg was compared to Modafinil 64 mg/kg and vehicle. : p<0.01; *: p<0.005, Two-Way ANOVA. (FIG. 6B) Oral treatment of Ox−/− male mice with flecainide 1 mg/kg was compared to vehicle.

Figure 7:
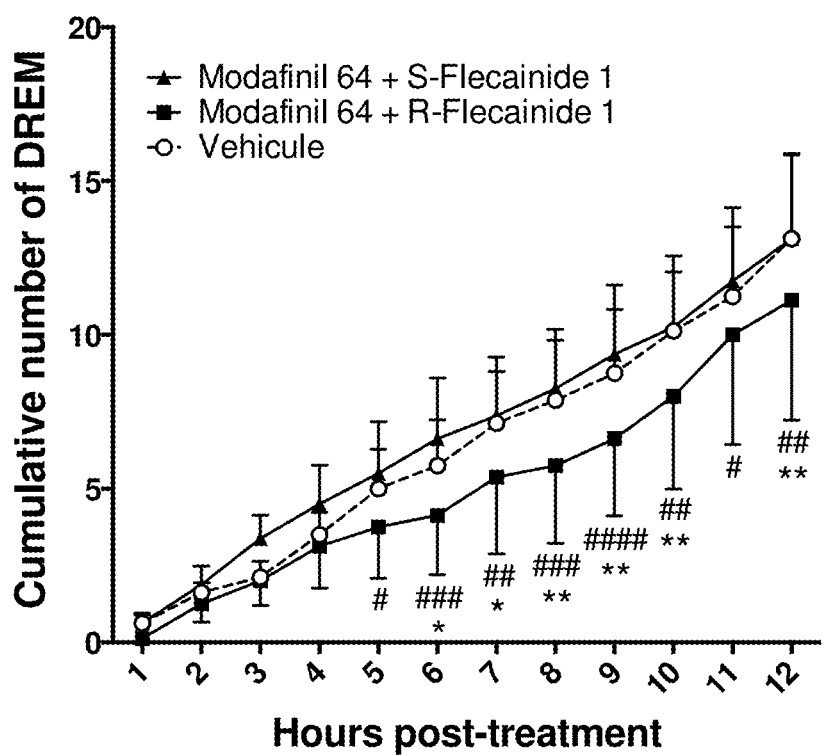

FIG. 7: Number of episodes of OREM/DREM phases in narcoleptic mice (Ox−/−) treated by the combination between modafinil and one of the two enantiomers of flecainide (R-flecainide and S-flecainide). Oral treatment with modafinil 64 mg/kg with R-flecainide 1 mg/kg or S-flecainide 1 mg/kg was compared to vehicle.

EXAMPLES

Example 1: Effect of Flecainide on Gap Junctions 1.1. Materials and Methods
Cell Culture The rat insulinoma RIN cell line, deficient in GJIC (del Corsso et al, 2006), was grown in OptiMem medium, supplemented with 10% fetal calf serum. GJB6 (Cx30), GJB1 (Cx32), GJB2 (Cx26), GJA5 (Cx40) and GJA1 (Cx43) open reading frames were amplified from human cDNA. The open reading frames were cloned in pcDNA3.1/V5-His-TOPO (Invitrogen). Cells were transfected using Lipofectamine and further selected using geneticin.

Dye Transfer Experiments

Cells were seeded and loaded with two fluorochromes, calcein acetoxymethyl ester, a gap junction permeable dye, and Vybrant DiI, a membrane lipophilic dye. The next day, cells were dissociated and incubated for four hours in presence of previously seeded non-loaded cells and in the presence of flecainide racemate 70, 140 or 280 µM, mefloquine 10 µM or meclofenamic acid (MFA) 100 µM. Flow cytometry was conducted on a FACScan. Inhibition was quantified as the relative number of receiver cells that gained fluorescence to the total number of receiver cells (non GJ-mediated dye transfer was then substracted to these ratio based on connexin non-expressing RIN cells, defined at background dye transfer ratio). This ratio of cellular coupling was then normalized, after each treatment, on the vehicle one.

Toxicity Analysis

Twenty thousand RIN were seeded in 100 µl of culture medium in 96-wells plates. After 48 h culture, cells were treated for 4 hours with previously identified chemical compounds at several concentrations. Cells were rinsed in PBS and grown 24 h in fresh medium. Cell viability was measured by using WST-1 (Roche).

1.2. Experimental Results

Cellular models were validated by using two classical inhibitors described in literature, meclofenamic acid (MFA) (Dhein, 2004) (100 µM) and mefloquine (Cruikshank et al, 2004) (10 µM). Results are shown on FIG. 1A. Flecainide is as efficient in blocking connexin as the other anti-connexin agents.

Cell viability tests (using WST-1, dotted curve on FIG. 1B) after one day of treatment, indicate that flecainide has no cell toxicity at the dose inhibiting cerebral connexins.

In addition, flecainide inhibits all the tested isoforms of cerebral connexin using dye-transfer cell-parachute assay (Cx30, Cx32, Cx26, Cx40, Cx43) (it is estimated that a more than a significant 10% reduction in gap junction cellular is considered as physiologically relevant). In addition, higher inhibition levels are reached for glial connexins Cx26, Cx30 and Cx43.

Example 2: Flecainide Potentiates the Waking Effects of Modafinil

Preclinical and clinical data indicated that modafinil modifies sleep-cycle rhythm and promotes wake phases (Lin et al, 2008). Here we tested in rodents whether such activity was potentiated by flecainide after oral challenge with modafinil, using polysomnographic analysis on implanted mice. Using a sub-efficient dosage of modafinil (32 mg/kg), the inventors demonstrated a new feature of the combination of modafinil and flecainide since it significantly increases the total duration of wake episodes.

2.1. Materials and Methods

Wild-type C57bl/6 male mice (n=9/groups) were implanted with EEG/EMG/EOG electrodes for polysomnographic analyses. After a two-week recovery period, mice were orally treated with vehicle, Modafinil 32 mg/kg and Modafinil 32 mg/kg+flecainide racemate 1 mg/kg and wake periods were quantified using Spike2 scripts. Here the inventors represented the duration of wake during the first three hours (after a one-hour period post-administration). **: $p<0.01$ in a One-Way ANOVA analysis.

2.2. Results

Modafinil is a molecule that promotes wakefulness in humans and mice, increasing in mice their activity in a dose-dependent manner (Simon et al, 1994). The activity of mice treated with modafinil at 32 mg/kg was compared with that of mice treated with the combination modafinil 32 mg/kg+flecainide 1 mg/kg or vehicle.

FIG. 2A shows that flecainide significantly increases the waking effects of modafinil. FIG. 2B shows that this effect is not mediated by flecainide alone.

Thus, flecainide significantly potentiates modafinil waking activity in wild type mice, while being devoid of own effect on wake duration.

Example 3: Flecainide Significantly Enhances Modafinil Cognitive Activity

Modafinil induces a cognitive enhancing effect (Beracochea et al, 2003), such property can be assessed using the alternating sequential test, a widely used apparatus to assess spatial working memory in mice (Beracochea & Jaffard, 1987). Spontaneous alternation is the innate tendency of rodents to alternate their choices to enter into the compartments of arrival of a T-maze device, over successive trials. To alternate during a given trial N, the animal must remember the choice made selectively in test N−1, and the response in alternating is performance measure. Acute administration of modafinil before entering the maze, can improve the performance of mice in this test (Beracochea et al, 2001). The inventors' results showed that flecainide significantly potentiates the promnesiant effect of a subefficient dose of modafinil, while flecainide alone is devoid of any own promnesiant effect.

3.1. Materials and Methods

The alternating sequential test is widely used to assess spatial working memory in mice (Beracochea & Jaffard, 1987). Spontaneous alternation is the innate tendency of rodents to alternate their choices to entry into the compartments of arrival of a T-maze device, over successive trials. To alternate during a given trial N, the animal must remember the choice made selectively in test N−1, so the decline in alternating will reflect the phenomenon of oblivion. The response in alternating is performance measure. Sequential alternating assesses more specifically the sensitivity to interference, a major factor in oblivion.

The experiment takes place in a T-maze (50 cm×10 cm×25 cm). All the subjects were given 7 successive trials separated by a 120-s intertrial interval. To begin a trial, the mouse was placed in the start box for 120 s before the door to the stem was opened. When the subject entered one of the goal arms, the door to that arm was closed. The chosen arm and the time that elapsed between opening the door and the arrival to the end of the chosen arm (task achievement time) were registered. Following a 30-s confinement period (fixed and invariant) in the chosen arm, the animal was removed and placed in the start box for a new trial. Between each test, the unit is cleaned with a cloth soaked in water and alcohol to avoid olfactory detection. The index memory is represented by the average of alternating percentage (number of alternation choices/total number of tests X 100). (n=6 to 23 for each group). Mice were intraperitoneally treated by either modafinil (64 mg/kg or 128 mg/kg) or modafinil (64 mg/kg) and flecainide racemate (1 mg/kg) or flecainide racemate alone (1 mg/kg) or vehicle.

$p<0.05$ in one sample t-test vs random 50% alternance;
* $p<0.05$ One way ANOVA followed by Tukey's multiple comparison vs modafinil group.

3.2. Results

The T-maze is a device for assessing working memory in mice. Acute administration of modafinil before entering the maze, can improve the performance of mice in this test (Beracochea et al, 2001).

The validity of the test was performed by comparing the responses of mice intraperitoneally treated with an effective dose of modafinil alone (128 mg/kg), a dose of flecainide alone (1 mg/kg) and a sub-effective dose of modafinil (64 mg/kg) with or without flecainide alone (1 mg/kg). The results are shown in FIG. 3.

These results show that flecainide significantly potentiates modafinil promnesiant activity, while flecainide alone shows no own cognitive effect.

Example 4: Flecainide Significantly Prolongs Modafinil Activity

Modafinil is a molecule that promotes wakefulness in humans and mice, increasing in mice their activity in a dose-dependent manner (Simon et al, 1994). The inventors' results showed that flecainide significantly potentiates the locomotor effect of a subefficient dose of modafinil, while flecainide alone is devoid of any own locomotor effect in rodents.

4.1. Materials and Methods

Mice (n=8 per batch) were orally treated by either modafinil (64 mg/kg) or modafinil (64 mg/kg) and flecainide racemate (1 mg/kg) or flecainide racemate alone (1 mg/kg) or vehicle and replaced in their home cage. Locomotor activity is evaluated by video tracking. Videos have been analyzed using Ethovision XT software (Noldus®).*: $p<0.01$ in a Two-Way ANOVA analysis 4.2. Results The activity of mice treated with modafinil at 64 mg/kg was compared with that of mice treated with the combination modafinil 64 mg/kg+flecainide 1 mg/kg. FIG. 4 shows that flecainide significantly increases the duration of effect of modafinil on the activity of mice.

To conclude, the above results show that Flecainide significantly inhibits the functionality of gap junctions, without inducing cellular toxicity. In addition, this compound potentiates the efficacy and duration of effect of modafinil, notably in its promnesiant and awakening side.

Example 5: Modafinil/Flecainide Combination has a Surprising Efficient Profile on DREM Cataplectic-Like Phenotype in Narcoleptic Mice 5.1. Material and Methods Animals Prepro-orexin knockout (KO) mice were offspring of the mouse strain generated by Chemelli et al. [1999] and kept on C57BL/6J genomic background. After backcrossing male orexin–/– mice and female wild-type (WT) mice for nine generations, the obtained orexin+/– mice were crossed to produce heterozygote and homozygote WT and KO littermates. To determine their genotypes with respect to orexin gene, tail biopsies were performed at the age of 4 weeks for DNA detection using PCR.

Surgery

At the age of 12 weeks and with a body weight of 30±2 g, mice used for EEG and sleep-wake studies were chronically implanted, under deep gas anesthesia using isoflurane (2%, 200 ml/min) and a TEM anesthesia system (Bordeaux, France), with six cortical electrodes (gold-plated tinned copper wire, Ø=0.4 mm, Filotex, Draveil, France) and three muscle electrodes (fluorocarbon-coated gold-plated stainless steel wire, Ø=0.03 mm, Cooner Wire Chatworth, Calif., U.S.A.) to record the electroencephalogram (EEG) and electromyogram (EMG) and to monitor the sleep-wake cycle. All electrodes were previously soldered to a multichannel electrical connector and each was separately insulated with a covering of heat-shrinkable polyolefin/polyester tubing. Cortical electrodes were inserted into the dura through 3 pairs of holes made in the skull, located respectively in the frontal (1 mm lateral and anterior to the bregma), parietal (1 mm lateral to the midline at the midpoint between the bregma and lambda), and occipital (2 mm lateral to the midline and 1 mm anterior to the lambda) cortex. Muscle electrodes were inserted into the neck muscles. Finally, the electrode assembly was anchored and fixed to the skull with Super-Bond (Sun Medical Co., Shiga, Japan) and dental cement. This implantation allows stable and long-lasting polygraphic recordings [Parmentier et al, 2002].

Polygraphic Recording in the Mouse and Data Acquisition and Analysis

After surgery, the animals were housed individually, placed in an insulated sound-proof recording room maintained at an ambient temperature of 23±1° C. and on a 12 h light/dark cycle (lights-on at 7 a.m.). After a 7-day recovery period, mice were habituated to the recording cable for 7 days before polygraphic recordings were started. Direct REM sleep onset (DREMs) episodes, also called narcoleptic episodes or sleep onset REM periods by some authors [Chemelli et al, 1999; Mignot et al, 2005; Fujiki et al, 2006], were defined as the occurrence of REM sleep directly from wake, namely a REM episode that follows directly a wake episode lasting more than 60 s without being preceded by any cortical slow activity of more that 5 s during the 60 s.

Drug Administration and Experimental Procedures in the Mouse

After recovery from the surgery and habituation to the recording cables, each mouse was subjected to a recording session of two continuous days, beginning at 7 a.m. Administrations were performed at 6:45 p.m. just before lights-off (7:00 p.m.), since orexin–/– mice display narcoleptic attacks only during lights-off phase [Chemelli et al, 1999]. The order of administration was randomized. Polygraphic recordings were made immediately after administration and were maintained during the whole lights-off period (12 h). Two administrations were separated by a period of 7 days (washout). Mice (n=8 per batch) were orally treated by either modafinil (64 mg/kg) or modafinil (64 mg/kg) and flecainide racemate (1 mg/kg) or flecainide racemate alone (1 mg/kg) or vehicle.

5.2. Results

Orexins (also known as hypocretins) are two hypothalamic neuropetides identified in 1998 [Sakurai et al, 1998; De Lecea L. et al, 1998]. Neurons containing orexins have been identified in the hypothalamic dorsolateral and perifornical areas, these neurons play a key role in behavioral arousal. A large body of evidence indicates that an orexin deficiency is responsible for the pathogenesis of human and animal narcolepsy [Lin et al, 1999; Chemelli et al, 1999]. It has been recently shown that the most major phenotypes of orexin KO mice are a behavior/motor deficit during waking and the occurrence, during the dark phase, of episodes of sleep onset REM (DREM, as known as SOREM)—defined on EEG, EMG and video recordings as sudden onset of paradoxical sleep directly from wakefulness [Anaclet et al, 2009]. Thus SOREM/DREM constitutes a main phenotype of murine narcolepsy which is frequently seen in narcoleptic patients [Lin et al, 20011]. Using this model, it was shown that modafinil allows DREM episodes to persist [Lin et al, 2008], a situation similar to that in the clinic in which modafinil improves excessive daytime sleepiness without clear effect in cataplexy.

Moreover, as disclosed on FIG. 6B, flecainide racemate (alone), at 1 mg/kg dose, has no effect on DREM cataplectic-like phenotype in narcoleptic Ox−/− mice.

However, and importantly, the results disclosed on FIG. 6A show that modafinil/flecainide combination decreases the occurrence of DREM episode.

Hence, flecainide and modafinil do not have any significant effect on a DREM cataplectic-like phenotype when used alone, whereas their combination importantly decreases the DREM cataplectic-like phenotype.

These results highlight the synergy existing between flecainide and modafinil, said synergy being due to the potentiation of the modafinil efficiency by flecainide, since no effect is seen with either modafinil or flecainide alone in narcoleptic mice.

Example 6: Modafinil/R-Flecainide is Surprisingly More Efficient than Modafinil/S-Flecainide on DREM Cataplectic-Like Phenotype in Narcoleptic Mice The same materials and methods than in example 5 were used, except that the flecainide racemate has been replaced by the R-flecainide enantiomer.

As disclosed on FIG. 7, R-flecainide enantiomer combined with modafinil is more efficient on DREM cataplectic-like phenotype in narcoleptic Ox−/− mice than the S-flecainide enantiomer combined with modafinil.

REFERENCES

S. Alessi-Severini, F. Jamali, F. M. Pasutto, R. T. Coutts, S. Gulamhusein, High-performance liquid chromatographic determination of the enantiomers of flecainide in human plasma and urine, J Pharm Sci 79 (1990) 257-260.

S. Alessi-Severini, D. F. LeGatt, F. M. Pasutto, F. Jamali, R. T. Coutts, HPLC analysis of flecainide enantiomers in plasma: comparison with fluorescence polarization immunoassay, Clin Chem 37 (1991) 111-112.

Anaclet C, Parmentier R, Ouk K, Guidon G, Buda C, Sastre J P, Akaoka H, Sergeeva O A, Yanagisawa M, Ohtsu H, Franco P, Haas H L, Lin J S (2009) Orexin/hypocretin and histamine: distinct roles in the control of wakefulness demonstrated using knock-out mouse models. *The Journal of neuroscience: the official journal of the Society for Neuroscience* 29: 14423-14438

E. H. Banitt, J. R. Schmid, R. A. Newmark, Resolution of flecainide acetate, N-(2-piperidylmethyl)-2,5-bis(2,2,2-trifluoroethoxy)benzamide acetate, and antiarrhythmic properties of the enantiomers, J Med Chem 29 (1986) 299-302.

Beracochea D, Cagnard B, Celerier A, le Merrer J, Peres M, Pierard C (2001) First evidence of a delay-dependent working memory-enhancing effect of modafinil in mice. *Neuroreport* 12: 375-378

Beracochea D, Celerier A, Peres M, Pierard C (2003) Enhancement of learning processes following an acute modafinil injection in mice. *Pharmacology, biochemistry, and behavior* 76: 473-479

Beracochea D J, Jaffard R (1987) Impairment of spontaneous alternation behavior in sequential test procedures following mammillary body lesions in mice: evidence for time-dependent interference-related memory deficits. *Behav Neurosci* 101: 187-197

M. I. Boulos M. I., B. J. Murray, Current evaluation and management of excessive daytime sleepiness, *Can J Neurol Sci* 37 (2010) 167-176

Chemelli R M, Willie J T, Sinton C M, Elmquist J K, Scammell T, Lee C, Richardson J A, Williams S C, Xiong Y, Kisanuki Y, Fitch T E, Nakazato M, Hammer R E, Saper C B, Yanagisawa M (1999) Narcolepsy in orexin knockout mice: molecular genetics of sleep regulation. *Cell* 98: 437-451

Cruikshank S J, Hopperstad M, Younger M, Connors B W, Spray D C, Srinivas M (2004) Potent block of Cx36 and Cx50 gap junction channels by mefloquine. *Proc Natl Acad Sci USA* 101: 12364-12369

Daleau P (1998) Effects of antiarrhythmic agents on junctional resistance of guinea pig ventricular cell pairs. *The Journal of pharmacology and experimental therapeutics* 284: 1174-1179

Dauvilliers Y., I. Arnulf, E. Mignot, Narcolepsy with cataplexy, *Lancet* 369 (2007) 499-511.

Davidson J O, Green C R, Nicholson L F, Bennet L, Gunn A J (2013) Connexin hemichannel blockade is neuroprotective after, but not during, global cerebral ischemia in near-term fetal sheep. *Experimental neurology* de Lecea L, Kilduff T S, Peyron C, Gao X, Foye P E, Danielson P E, Fukuhara C, Battenberg E L, Gautvik V T, Bartlett F S, 2nd, Frankel W N, van den Pol A N, Bloom F E, Gautvik K M, Sutcliffe J G (1998) The hypocretins: hypothalamus-specific peptides with neuroexcitatory activity. *Proc Natl Acad Sci USA* 95: 322-327 del Corsso C, Srinivas M, Urban-Maldonado M, Moreno A P, Fort A G, Fishman G I, Spray D C (2006) Transfection of mammalian cells with connexins and measurement of voltage sensitivity of their gap junctions. *Nat Protoc* 1: 1799-1809

Dhein S (2004) Pharmacology of gap junctions in the cardiovascular system. *Cardiovasc Res* 62: 287-298

Dubey S, Ahi S, Reddy I M, Kaur T, Beotra A, Jain S (2009) A novel study of screening and confirmation of modafinil, adrafinil and their metabolite modafinilic acid under EI-GC-MS and ESI-LC-MS-MS ionization. *Indian journal of pharmacology* 41: 278-283

Durham P L, Garrett F G (2009) Neurological mechanisms of migraine: potential of the gap-junction modulator tonabersat in prevention of migraine. *Cephalalgia* 29 Suppl 2: 1-6

N. Fujiki, Y. Yoshida, S. Zhang, T. Sakurai, M. Yanagisawa, S. Nishino, Sex difference in body weight gain and leptin signaling in hypocretin/orexin deficient mouse models, Peptides 27 (2006) 2326-2331.

Gotter A L, Webber A L, Coleman P J, Renger J J, Winrow C J (2012) International Union of Basic and Clinical Pharmacology. LXXXVI. Orexin receptor function, nomenclature and pharmacology. *Pharmacological reviews* 64: 389-420

A. S. Gross, G. Mikus, C. Fischer, R. Hertrampf, U. Gundert-Remy, M. Eichelbaum, Stereoselective disposition of flecainide in relation to the sparteine/debrisoquine metaboliser phenotype, Br J Clin Pharmacol 28 (1989) 555-566.

K. Hanada, S. Akimoto, K. Mitsui, M. Hashiguchi, H. Ogata, Quantitative determination of disopyramide, verapamil and flecainide enantiomers in rat plasma and tissues by high-performance liquid chromatography, J Chromatogr B Biomed Sci Appl 710 (1998) 129-135.

Harks E G, de Roos A D, Peters P H, de Haan L H, Brouwer A, Ypey D L, van Zoelen E J, Theuvenet A P (2001) Fenamates: a novel class of reversible gap junction blockers. *The Journal of pharmacology and experimental therapeutics* 298: 1033-1041

Ishizuka T, Murotani T, Yamatodani A (2012) Action of modafinil through histaminergic and orexinergic neurons. *Vitamins and hormones* 89: 259-278

Juszczak G R, Swiergiel A H (2009) Properties of gap junction blockers and their behavioural, cognitive and electrophysiological effects: animal and human studies. *Prog Neuropsychopharmacol Biol Psychiatry* 33: 181-198

H. K. Kroemer, J. Turgeon, R. A. Parker, D. M. Roden, Flecainide enantiomers: disposition in human subjects and electrophysiologic actions in vitro, Clin Pharmacol Ther 46 (1989) 584-590

Laird D W (2006) Life cycle of connexins in health and disease. *Biochem J* 394: 527-543

A. H. L. Lie, R. M. Stuurman, F. N. Ijdenberg, J. H. Kingma, D. K. Meijer, High-performance liquid chromatographic assay of flecainide and its enantiomers in serum, Ther Drug Monit 11 (1989) 708-711.

A. H. L. Lie, J. van den Akker, A. den Hertog, D. K. Meijer, The action of flecainide acetate and its enantiomers on mammalian non-myelinated nerve fibres, Pharm Weekbl Sci 11 (1989) 92-94.

J. S. Lin, C. Anaclet, O. A. Sergeeva, H. L. Haas, The waking brain: an update, Cell Mol Life Sci 68 (2011) 2499-2512.

Lin J S, Dauvilliers Y, Arnulf I, Bastuji H, Anaclet C, Parmentier R, Kocher L, Yanagisawa M, Lehert P, Ligneau X, Perrin D, Robert P, Roux M, Lecomte J M, Schwartz J C (2008) An inverse agonist of the histamine H(3) receptor improves wakefulness in narcolepsy: studies in orexin-/- mice and patients. *Neurobiology of disease* 30: 74-83

Lin J S, Sergeeva O A, Haas H L (2011) Histamine H3 receptors and sleep-wake regulation. *The Journal of pharmacology and experimental therapeutics* 336: 17-23

Lin L, Faraco J, Li R, Kadotani H, Rogers W, Lin X, Qiu X, de Jong P J, Nishino S, Mignot E (1999) The sleep disorder canine narcolepsy is caused by a mutation in the hypocretin (orexin) receptor 2 gene. *Cell* 98: 365-376

R. Mehvar, D. R. Brocks, M. Vakily, Impact of stereoselectivity on the pharmacokinetics and pharmacodynamics of antiarrhythmic drugs, Clin Pharmacokinet 41 (2002) 533-558.

E. Mignot, S. Nishino, Emerging therapies in narcolepsy-cataplexy, Sleep 28 (2005) 754-763.

Minzenberg M J, Carter C S (2008) Modafinil: a review of neurochemical actions and effects on cognition. *Neuropsychopharmacology* 33: 1477-1502

Nakase T, Naus C C (2004) Gap junctions and neurological disorders of the central nervous system. *Biochim Biophys Acta* 1662: 149-158

R. Parmentier, H. Ohtsu, Z. Djebbara-Hannas, J. L. Valatx, T. Watanabe, J. S. Lin, Anatomical, physiological, and pharmacological characteristics of histidine decarboxylase knock-out mice: evidence for the role of brain histamine in behavioral and sleep-wake control, J Neurosci 22 (2002) 7695-7711.

Patel S J, Milwid J M, King K R, Bohr S, Iracheta-Velle A, Li M, Vitalo A, Parekkadan B, Jindal R, Yarmush M L (2012) Gap junction inhibition prevents drug-induced liver toxicity and fulminant hepatic failure. *Nature biotechnology* 30: 179-183

Sakurai T, Amemiya A, Ishii M, Matsuzaki I, Chemelli R M, Tanaka H, Williams S C, Richarson J A, Kozlowski G P, Wilson S, Arch J R, Buckingham R E, Haynes A C, Carr S A, Annan R S, McNulty D E, Liu W S, Terrett J A, Elshourbagy N A, Bergsma D J, Yanagisawa M (1998) Orexins and orexin receptors: a family of hypothalamic neuropeptides and G protein-coupled receptors that regulate feeding behavior. *Cell* 92: 1 page following 696

Simon P, Panissaud C, Costentin J (1994) The stimulant effect of modafinil on wakefulness is not associated with an increase in anxiety in mice. A comparison with dexamphetamine. *Psychopharmacology (Berl)* 114: 597-600

J. K. Smallwood, D. W. Robertson, M. I. Steinberg, Electrophysiological effects of flecainide enantiomers in canine Purkinje fibres, Naunyn Schmiedebergs Arch Pharmacol 339 (1989) 625-629.

Takeuchi H, Mizoguchi H, Doi Y, Jin S, Noda M, Liang J, Li H, Zhou Y, Mori R, Yasuoka S, Li E, Parajuli B, Kawanokuchi J, Sonobe Y, Sato J, Yamanaka K, Sobue G, Mizuno T, Suzumura A (2011) Blockade of gap junction hemichannel suppresses disease progression in mouse models of amyotrophic lateral sclerosis and Alzheimer's disease. *PLoS One* 6: e21108

Tong X, Dong S, Yu M, Wang Q, Tao L (2013) Role of heteromeric gap junctions in the cytotoxicity of cisplatin. *Toxicology* 310C: 53-60

Traynelis S F, Wollmuth L P, McBain C J, Menniti F S, Vance K M, Ogden K K, Hansen K B, Yuan H, Myers S J, Dingledine R (2010) Glutamate receptor ion channels: structure, regulation, and function. *Pharmacological reviews* 62: 405-496

J. Turgeon, H. K. Kroemer, C. Prakash, I. A. Blair, D. M. Roden, Stereoselective determination of flecainide in human plasma by high-performance liquid chromatography with fluorescence detection, J Pharm Sci 79 (1990) 91-95.

What is claimed is:

1. A method for potentiating the effects of a psychotropic drug in a patient in need thereof, said method comprising administration of flecainide and at least one psychotropic drug, wherein the psychotropic drug is not flupirtine in said patient.

2. The method of claim 1, wherein said psychotropic drug is selected from the group consisting of GABAergic, dopaminergic, norepinephrinergic, serotoninergic, histaminergic, and glutamatergic effectors, and those having an effect on the hypocretin/orexin system.

3. The method of claim 1, wherein said psychotropic drug is selected from the group consisting of caffeine, mazindol, sodium oxybate, pitolisant, amphetamine, methylphenidate, (R)-(beta-amino-benzenepropyl) carbamate mono-hydrochloride, and armodafinil.

4. The method of claim 1, wherein said flecainide is the R enantiomer of formula:

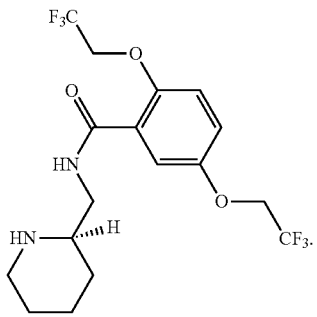 [SMILES: O=C(NC[C@H]1CCCCN1)c1cc(OCC(F)(F)F)ccc1OCC(F)(F)F]

5. A therapeutic composition comprising flecainide and at least one psychotropic drug, wherein said psychotropic drug is not flupirtine.

6. The therapeutic composition according to claim 5, wherein said psychotropic drug is selected from the group consisting of GABAergic, dopaminergic, norepinephrinergic, serotoninergic, histaminergic, and glutamatergic effectors, and those having an effect on the hypocretin/orexin system.

7. The therapeutic composition according to claim 5, wherein said psychotropic drug is selected from the group consisting of caffeine, mazindol, sodium oxybate, pitolisant, amphetamine, methylphenidate, (R)-(beta-amino-benzenepropyl) carbamate mono-hydrochloride, and armodafinil.

8. The therapeutic composition according to claim 5, wherein said flecainide is the R enantiomer of formula:

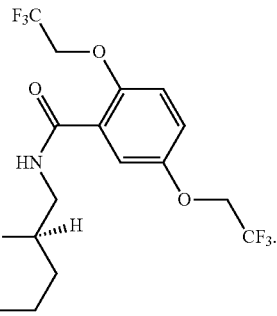

* * * * *